(12) United States Patent
Raso

(10) Patent No.: US 7,413,884 B2
(45) Date of Patent: *Aug. 19, 2008

(54) IMMUNOLOGICAL CONTROL OF β-AMYLOID LEVELS IN VIVO

(75) Inventor: Victor Raso, Brighton, MA (US)

(73) Assignee: Boston Biomedical Research Institute, Watertown, MA (US)

( * ) Notice: Subject to any disclaimer, the term of this patent is extended or adjusted under 35 U.S.C. 154(b) by 555 days.

This patent is subject to a terminal disclaimer.

(21) Appl. No.: 10/385,065

(22) Filed: Mar. 10, 2003

(65) Prior Publication Data

US 2003/0235897 A1  Dec. 25, 2003

Related U.S. Application Data

(63) Continuation of application No. 09/594,366, filed on Jun. 15, 2000, now Pat. No. 6,582,945.

(60) Provisional application No. 60/139,408, filed on Jun. 16, 1999.

(51) Int. Cl.
*C12N 9/00* (2006.01)
*C07K 16/00* (2006.01)
*G01N 33/53* (2006.01)

(52) U.S. Cl. ............. 435/188.5; 435/7.92; 435/116; 435/69.1

(58) Field of Classification Search ............. 435/188.5
See application file for complete search history.

(56) References Cited

U.S. PATENT DOCUMENTS

| | | | |
|---|---|---|---|
| 5,190,865 A * | 3/1993 | Schultz | 435/108 |
| 5,439,812 A | 8/1995 | Benkovic et al. | |
| 5,900,237 A | 5/1999 | Napper et al. | |
| 6,043,069 A | 3/2000 | Koentgen et al. | |
| 6,140,091 A | 10/2000 | Raso et al. | |
| 6,294,374 B1 * | 9/2001 | Sinha et al. | 435/280 |
| 6,329,508 B1 | 12/2001 | Friden | |
| 6,702,705 B1 | 3/2004 | von Borstel et al. | |
| 6,710,226 B1 | 3/2004 | Schenk | |
| 6,743,427 B1 | 6/2004 | Schenk | |
| 6,750,324 B1 | 6/2004 | Schenk et al. | |

2004/0081657 A1  4/2004  Schenk

FOREIGN PATENT DOCUMENTS

| | | |
|---|---|---|
| WO | WO 99/06066 | 2/1999 |
| WO | WO 99/06536 | 2/1999 |
| WO | WO 99/27944 | 6/1999 |

OTHER PUBLICATIONS

Janda, K.D., et al. (1991) Tetrahedron 47(14/15), 2503-2506.*
Yu, J., et al. (1994) Angew. Chem. Int. Ed. Engl. 33(3), 339-340.*
Tawfik, D.S., et al. (1994) Molecular Biotech. 1, 87-103.*
Iazo et al. Protein sci. 2005, 1581-1596.*
Hardy, J., Nature Genetics 1: 233-234 (1992).
Scheuner et al., Nature Med. 2: 864-870 (1996).
Kowall et al., Proc. Natl. Acad. Sci. USA 88: 7247-7251 (1991).
Gravina et al., J. of Biol. Chem. 270: 7013-7016 (1995).
Bickel et al., Proc. Natl. Acad. Sci. USA 90: 2618-2622 (1993).
Broadwell et al., Exp. Neurol. 142: 47-65 (1996).
Saito et al., Proc. Natl. Acad. Sci. USA 92: 10227-10231 (1995).
Pardridge et al., Pharmaceutical Res. 12: 807-816 (1995).
Descamps et al., Am. J. Physiol. 270: H1149-H1158 (1996).
Duffy and Pardridge, Brain Res. 420: 32-38 (1987).
Dehouck et al., J. Cell Biol. 138: 877-889 (1997).
Raso et al., J. Biol. Chem. 272: 27623-27628 (1997).
Mallander and Voss, J. Biol. Chem. 269: 199-206 (1994).
Kang and Pardridge, J. Pharm. Exp. Ther. 269:344-350 (1994).
Recht et al., J. Neurosurg. 72: 941-945 (1990).
Solomon et al., Proc. Natl. Acad. Sci. USA 94: 4109-4112 (1997).
Shin et al., Proc. Natl. Acad. Sci. USA 92: 2820-2824 (1995).

* cited by examiner

*Primary Examiner*—Tekchand Saidha
*Assistant Examiner*—Md. Younus Meah
(74) *Attorney, Agent, or Firm*—Pierce Atwood LLP; Kevin M. Farrell; David J. Wilson

(57) ABSTRACT

Disclosed are antibodies which catalyze hydrolysis of β-amyloid. Antibodies generated are characterized by the amide linkage which they hydrolyze. Methods of generating the antibodies by using β-amyloid peptides which incorporate transition state analogs are also provided. Also disclosed is a vectorized antibody which is characterized by the ability to cross the blood brain barrier, and is further characterized by the ability to catalyze the hydrolysis of β-amyloid. The vectorized antibody can take the form of bispecific antibody, which has a first specificity for the transferrin receptor and a second specificity for a taransition state adopted by β-amyloid hydrolysis.

8 Claims, 13 Drawing Sheets

H₂N-DAEFRHDSGYEVHHQKLVFFAEDVGSNKGAIIGLMVGGVVIAT-CO₂H (SEQ ID NO:1)
1          10          20          30          40

FIG. 1

H₂N-Asp-Ala-Glu-Phe-Arg-His-Asp-Ser-Gly-Tyr-Glu-Val-His-His-Gln-Lys-Cys-amide (SEQ ID NO:2)
1                   5                   10                  15

FIG. 2

Cys-Tyr-Glu-Val-His-His-Gln-Lys-Leu-Val-Phe-Phe-Ala-Glu-Asp-Val-Gly-amide (SEQ ID NO:3)
      10                  15                  20                  25

FIG. 3

Cys-Met-Val-Gly-Gly-Val-Val-Ile-Ala-Thr-CO₂H (SEQ ID NO:4)
35                  40

FIG. 4

Cys-Tyr-Glu-Val-His-His-Gln-Lys-Leu-Val-Phe-Phe-Ala-Glu-Asp-Val-Gly-Gly-amide
 10                          15                              20                          25

FIG. 7

Cys-Met-Val-Gly-Gly-Val-Val-Ile-Ala-Thr-CO₂H
 35                          40

FIG. 6

N-acetyl-Cys-Met-Val-Gly-Gly-CO-NH-Val-Val-Ile-Ala-amide
35 ↓ 40

N-acetyl-Cys-Met-Val-Gly-Gly-PO₂⁻-NH-Val-Val-Ile-Ala-amide

*FIG. 10*

IMMUNOLOGICAL CONTROL OF β-AMYLOID LEVELS IN VIVO

BACKGROUND OF THE INVENTION

Alzheimer's disease is a progressive and ultimately fatal form of dementia that affects a substantial portion of the elderly population. Definitive diagnosis at autopsy relies on the presence of neuropathological brain lesions marked by a high density of senile plaques. These extracellular deposits are found in the neo-cortex, hippocampus and amygdala as well as in the walls of the meningeal and cerebral blood vessels. The principal component of these plaques is a 39 to 43 residue β-amyloid peptide. Each plaque contains approximately 20 fmole (80 picograms) of this 4 kDa peptide (Selkoe et al., *J. of Neurochemistry* 46: 1820 (1986)). Apolipoprotein E and neurofibrillary tangles formed by the microtubule-associated tau protein are also often associated with Alzheimer's disease.

β-amyloid is proteolytically cleaved from an integral membrane protein called the β-amyloid precursor protein. The gene which codes for this protein in humans is found on chromosome 21 (St George-Hyslop et al., *Science* 235: 885 (1987), Kang et al., *Nature* 325: 733 (1987)). Numerous cultured cells and tissues (eg. brain, heart, spleen, kidney and muscle) express this β-amyloid precursor protein and also secrete the 4 kDa β-amyloid fragment into culture media, apparently as part of a normal processing pathway.

While it is difficult to establish an absolute causal relationship between β-amyloid or the plaques it forms and Alzheimer's disease, there is ample evidence to support the pathogenic role of β-amyloid. For example, patients with Down's syndrome have an extra copy of the β-amyloid precursor protein gene due to trisomy of chromosome 21 (St George-Hyslop et al., *Science* 235: 885 (1987), Kang et al., *Nature* 325: 733 (1987)). They correspondingly develop an early-onset Alzheimer's disease neuropathology at 30-40 years of age. Moreover, early-onset familial Alzheimer's disease can result from mutations in the β-amyloid precursor protein gene which fall within or adjacent to the β-amyloid sequence (Hardy, J., *Nature Genetics* 1: 233 (1992)). These observations are consistent with the notion that deposition of β-amyloid as plaques in the brain are accelerated by an elevation in its extracellular concentration (Scheuner et al., *Nature Med.* 2: 864 (1996)). The finding that β-amyloid is directly neurotoxic both in vitro and in vivo (Kowall et al., *Proc. Natl. Acad. Sci.* 88: 7247 (1991)), suggest that soluble aggregated β-amyloid, not the plaques per se, may produce the pathology.

Observations have indicated that amyloid plaque formation may proceed by a crystallization type mechanism (Jarrett et al., *Cell* 73: 1055 (1993)). According to this model, the seed that initiates plaque nucleation is an β-amyloid which is 42 or 43 amino acids long ($A\beta_{1-43}$). The rate-determining nucleus formed by $A\beta_{1-43}$ or $A\beta_{1-42}$ allows peptides $A\beta_{1-40}$ or shorter to contribute to the rapid growth of an amyloid deposit. This nucleation phenomenon was demonstrated in vitro by the ability of $A\beta_{1-42}$ to cause the instantaneous aggregation of a kinetically stable, supersaturated solution of $A\beta_{1-40}$. That finding has led to the possibility that $A\beta_{1-40}$ might be relatively harmless in the absence of the nucleation peptides $A\beta_{1-42}$ or $A\beta_{1-43}$. Indeed, elevated levels of these long peptides have been found in the blood of patients with familial Alzheimer's disease (Scheuner et al., *Nature Med.* 2: 864 (1996)). Moreover, $A\beta_{1-42}$ or $A\beta_{1-43}$ was found to be the predominant form deposited in the brain plaques of many Alzheimer's disease patients (Gravina et al., *J. of Biol. Chem.* 270: 7013 (1995)).

Given the central role played by β-amyloid, it has become increasingly important to understand the interrelationship between the different pools of these molecules in the body. Free β-amyloid present in the blood most likely arises from peptide released by proteolytic cleavage of β-amyloid precursor protein present on cells in the peripheral tissues. Likewise most of the free β-amyloid found in the brain and cerebrospinal fluid is probably derived from peptide released by secretase cleavage of β-amyloid precursor protein expressed on brain cells. The peptides are identical regardless of origin, and the results from several studies suggest an intercommunication between these pools.

SUMMARY OF THE INVENTION

One aspect of the present invention is an antibody which catalyzes hydrolysis of β-amyloid at a predetermined amide linkage. In one embodiment, the antibody preferentially binds a transition state analog which mimics the transition state adopted by β-amyloid during hydrolysis at a predetermined amide linkage and also binds to natural β-amyloid with sufficient affinity to detect using an ELISA. In another embodiment, the antibody preferentially binds a transition state analog which mimics the transition state adopted by β-amyloid during hydrolysis at a predetermined amide linkage, and does not bind natural β-amyloid with sufficient affinity to detect using an ELISA. Antibodies generated are characterized by the amide linkage which they hydrolyze. Specific antibodies include those which catalyze the hydrolysis at the amyloid linkages between residues 39 and 40, 40 and 41, and 41 and 42, of β-amyloid.

Another aspect of the present invention is a vectorized antibody which is characterized by the ability to cross the blood brain barrier and is also characterized by the ability to catalyze the hydrolysis of β-amyloid at a predetermined amide linkage. In one embodiment, the vectorized antibody is a bispecific antibody. Preferably, the vectorized antibody has a first specificity for the transferrin receptor and a second specificity for a transition state adopted by β-amyloid during hydrolysis. Specific vectorized antibodies include those which catalyze the hydrolysis at the amyloid linkages between residues 39 and 40, 40 and 41, and 41 and 42, of β-amyloid.

Another aspect of the present invention is a method for sequestering free β-amyloid in the bloodstream of an animal by intravenously administering antibodies specific for β-amyloid to the animal in an amount sufficient to increase retention of β-amyloid in the circulation. Therapeutic applications of this method include treating patients diagnosed with, or at risk for Alzheimer's disease.

Another aspect of the present invention is a method for sequestering free β-amyloid in the bloodstream of an animal by immunizing an animal with an antigen comprised of an epitope which is present on β-amyloid endogenous to the animal under conditions appropriate for the generation of antibodies which bind endogenous β-amyloid. Therapeutic applications of this method include treating patients diagnosed with, or at risk for Alzheimer's disease.

Another aspect of the present invention is a method for reducing levels of β-amyloid in the brain of an animal by intravenously administering antibodies specific for endogenous β-amyloid to the animal in an amount sufficient to increase retention of β-amyloid in the circulation of the animal. In one embodiment, the antibodies are catalytic antibodies which catalyze hydrolysis of β-amyloid at a predetermined amide linkage. The antibodies may be either monoclonal or polyclonal. In one embodiment, the antibodies specifically recognize epitopes on the C-terminus of β-amyloid$_{1-43}$.

Another aspect of the present invention is a method for reducing levels of β-amyloid in the brain of an animal, by immunizing the animal with an antigen comprised of an epitope which is present on endogenous β-amyloid under conditions appropriate for the generation of antibodies which bind endogenous β-amyloid. In one embodiment, the antigen is a transition state analog which mimics the transition state adopted by β-amyloid during hydrolysis at a predetermined amide linkage. In a preferred embodiment, the antigen is comprised of Aβ$_{10-25}$. Preferably, the antibodies generated have a higher affinity for the transition state analog than for natural β-amyloid, and catalyze hydrolysis of endogenous β-amyloid.

Similar methods which utilize or generate antibodies which catalyze the hydrolysis of β-amyloid for reducing levels of circulating β-amyloid in an animal, and also for preventing the formation of amyloid plaques in the brain of an animal, are also provided. Also, methods for disaggregating amyloid plaques present in the brain of an animal by utilizing or generating antibodies which catalyze the hydrolysis of β-amyloid are provided.

Another aspect of the present invention is a method for disaggregating amyloid plaques present in the brain of an animal by intravenously administering vectorized bispecific antibodies to the animal in an amount sufficient to cause significant reduction in β-amyloid levels in the brain of the animal. The vectorized bispecific antibodies are competent to transcytose across the blood brain barrier, and have the ability to catalyze hydrolysis of endogenous β-amyloid at a predetermined amide linkage upon binding. Preferably, the vectorized bispecific antibodies specifically bind the transferrin receptor.

Another aspect of the present invention is a method for generating antibodies which catalyze hydrolysis of a protein or polypeptide by immunizing an animal with an antigen comprised of an epitope which has a statine analog which mimics the conformation of a predetermined hydrolysis transition state of the polypeptide, under conditions appropriate for the generation of antibodies to the hydrolysis transition state. This method can be used to generate catalytic antibodies to β-amyloid. A similar method, which utilizes reduced peptide bond analogs to mimic the conformation of a hydrolysis transition state of a polypeptide, is also provided.

BRIEF DESCRIPTION OF THE FIGURES

FIG. 1 is an amino acid sequence listing (SEQ ID NO: 1) of the 43 residue β-amyloid peptide (Aβ).

FIG. 2 is an amino acid sequence listing (SEQ ID NO: 2) of the antigenic peptide made from the N-terminal sequence of β-amyloid (Aβ$_{1-16}$)

FIG. 3 is an amino acid sequence listing (SEQ ID NO: 3) of the antigenic peptide made from the central region of β-amyloid (Aβ$_{10-25}$).

FIG. 4 is an amino acid sequence listing (SEQ ID NO: 4) (Aβ$_{35-43}$) of the antigenic peptide made from the C-terminal sequence of β-amyloid.

FIG. 6 indicates the amide linkages in the peptide made from the β-amyloid C-terminal sequence (SEQ ID NO: 4) that were independently or concurrently replaced with a statyl moiety, to generate the different statine transition state analogs of the peptide.

FIG. 7 indicates the amide linkages in the peptide made from the β-amyloid central sequence (SEQ ID NO: 3) that were independently or concurrently replaced with a phenylalanine statine moiety, to generate the different phenylalanine statine transition state analogs of the peptide.

FIG. 10 is a formulaic representation of the native C-terminal region of β-amyloid, and the phosphonamidate transition state analog of the C-terminal region of β-amyloid (Aβ$_{35-43}$).

DETAILED DESCRIPTION OF THE INVENTION

Figure 5:
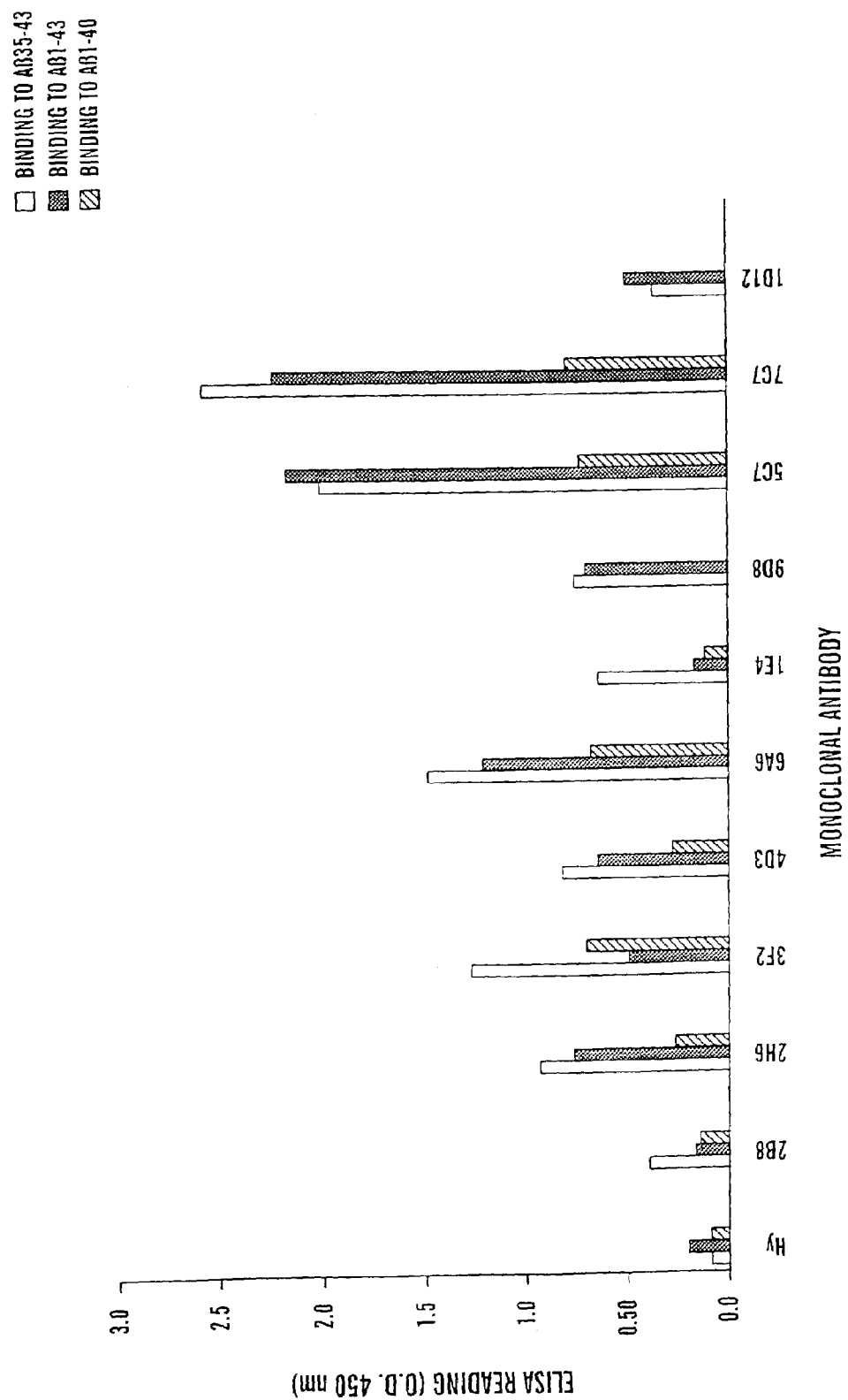
FIG. 5 is a diagrammatic representation of data from an ELISA comparing monoclonal antibody binding to Aβ$_{35-43}$ and Aβ$_{1-43}$ versus Aβ$_{1-40}$.

The present invention relates to immunologically based methods for controlling levels of β-amyloid in the body of an animal. The invention is based on the finding that antibodies specific for β-amyloid are able to bind β-amyloid in the presence of a physiological level of human serum albumin. The invention is also based on the finding that an animal can tolerate the presence of antibodies specific for β-amyloid in amounts sufficient to sequester β-amyloid in the bloodstream.

One aspect of the present invention relates to a method for sequestering free β-amyloid in the bloodstream of an animal. The soluble and insoluble forms of β-amyloid present within an animal are in dynamic equilibrium. Soluble β-amyloid is thought to translocate between blood and cerebrospinal fluid. Insoluble β-amyloid aggregates deposit from the soluble pool in the brain, as amyloid plaques. Results detailed in the Exemplification section below indicate that intravenous administration of antibodies specific for β-amyloid to an animal impedes the passage of soluble β-amyloid out of the peripheral circulation. This occurs because the β-amyloid specific antibodies, which are restricted to the peripheral circulation, bind to β-amyloid and sequester it in the circulation. Such sequestration is accomplished through intravenous administration of an appropriate amount of antibodies specific for β-amyloid to the animal. The amount of antibody which is sufficient to produce sequestration is dependent upon various factors (e.g., specific characteristics of the antibody to be delivered, the size, metabolism, and overall health of the animal) and are to be determined on a case by case basis.

Administered antibodies can be monoclonal antibodies, a mixture of different monoclonal antibodies, polyclonal antibodies, or any combination therein. In one embodiment, the antibodies bind to the C-terminal region of β-amyloid. Such antibodies specifically bind the less abundant, but more noxious $A\beta_{1-43}$ species in the blood as opposed to the smaller and less detrimental $A\beta_{1-40}$. In another embodiment, a combination of antibodies having specificity for various regions of β-amyloid are administered. In another embodiment, antibodies which catalyze the hydrolysis of β-amyloid, discussed in more detail below, are administered either alone or in combination with other anti-β-amyloid antibodies.

The animal to which the antibodies are administered is any animal which has circulating soluble β-amyloid. In one embodiment, the animal is a human. The human may be a healthy individual, or alternatively, may be suffering from or at risk for a disease in which elevated β-amyloid levels are thought to play a role, for example a neurodegenerative disease such as Alzheimer's disease.

A related aspect of the present invention is a method for sequestering free β-amyloid in the bloodstream of an animal by stimulating an immune response within the animal to endogenous β-amyloid. The results detailed in the Exemplification below indicate that an animal can tolerate the induction of an immune response which produces antibodies to endogenous β-amyloid, and that the presence of such antibodies will alter the distribution of β-amyloid in the body, in a similar manner as the above described method of administering β-amyloid binding antibodies. The immune response to endogenous β-amyloid is generated by immunizing the animal with one or more antigens comprised of epitopes present on the endogenous β-amyloid. Epitopes present on the inoculated antigens can correspond to epitopes present on any region of the β-amyloid molecule. In a preferred embodiment, epitopes found on the C-terminal region of β-amyloid are used to generate antibodies which specifically bind the $A\beta_{1-43}$ species as opposed to the smaller $A\beta_{1-40}$. In an alternate embodiment, a combination of different epitopes are administered to generate a variety of antibodies to β-amyloid. A more generalized immune response is generated by immunizing either with a mixture of different small peptide antigens or with the full-length 43 residue β-amyloid peptide. In another embodiment, antigens used for inoculation include transition state analogs of β-amyloid peptides to induce antibodies which have catalytic activity directed towards β-amyloid hydrolysis, described in detail below.

The immunoreactivity of the antigens can be enhanced by a variety of methods, many of which involve coupling the antigen to an immunogenic carrier. In addition, various methods are known and available to one of skill in the art for specifically enhancing the immunogenicity of endogenous molecules or the epitopes contained therein. Various modifications can be made to the β-amyloid antigen(s) described herein to render it more compatible for human use. For example, the peptide(s), can be genetically engineered into appropriate antigenic carriers, or DNA vaccines can be designed.

The above techniques for sequestering β-amyloid in the circulation are also useful for reducing the levels of β-amyloid in the brain. Because the formation of amyloid plaques in the brain is dependent, at least in part, on the levels of free β-amyloid present in the brain, reducing brain β-amyloid levels of an animal will, in turn, reduce the formation of amyloid plaques in the brain. Therefore, the above techniques are useful for preventing the formation of amyloid plaques in the brain of an animal. This is especially applicable to an animal which is considered at risk for the development of amyloid plaques; a risk which may result from a genetic predisposition or from environmental factors. Administration of antibodies, or immunization of the animal to produce endogenous antibodies, to β-amyloid can be of therapeutic benefit to such an animal (e.g., a human who has a family history of Alzheimer's disease, or who is diagnosed with the disease).

Another aspect of the present invention relates to antibodies which are characterized by the ability to catalyze the hydrolysis of β-amyloid at a predetermined amide linkage. Experiments detailed in the Exemplification section demonstrate the generation of different antibodies which have proteolytic activity towards β-amyloid. Such antibodies are generated by immunizing an animal with an antigen which is a transition state analog of the β-amyloid peptide. A transition state analog mimics the transition state that β-amyloid adopts during hydrolysis of a predetermined amide linkage. Transition state analogs useful for generating the catalytic antibodies include, without limitation, statine, phenylalanine statine, phosphonate, phosphonamidate, and reduced peptide bond transition state analogs.

Antibodies generated to epitopes unique to the transition state preferentially bind β-amyloid in the transition state. Binding of these antibodies stabilizes the transition state, which leads to hydrolysis of the corresponding amide bond. The particular amide linkage to be hydrolyzed is chosen based upon the desired cleavage product. For example, cleavage of full length β-amyloid into two peptide fragments which cannot aggregate into amyloid plaques would be of therapeutic use in the methods disclosed herein. Antibodies may be either monoclonal or polyclonal. Several such transition state mimics have been made and used as antigen in the generation of monoclonal antibodies which catalyze the cleavage at the indicated linkage. These antigens and the antibodies generated are listed in Table 8 of the Exemplification section below. Antibodies generated to antigens which have transition state mimics incorporated at a specific amide linkage, should bind the natural hydrolysis transition states of these linkages in native β-amyloid, stabilizing the transition state and catalyzing cleavage at that linkage.

At least two different classes of antibodies are generated by the above methods. The first class preferentially binds the transition state analog, and also detectably cross reacts with natural β-amyloid using the ELISA detailed in the Exemplification section, to detect binding. The second class binds the transition state analog, and does not detectably cross react with natural β-amyloid using the ELISA procedure detailed in the Exemplification section to detect binding. Both classes of antibodies have potential value as catalytic antibodies. The respective binding affinities of an anti-transition state antibody is likely to reflect its activity at catalyzing hydrolysis. It is thought that in order for an antibody to have activity at catalyzing hydrolysis of a protein, it must possess at least a minimal ability to bind the natural (non-transition) state of the protein. Antibodies which retain significant binding for β-amyloid, (that strongly cross react with natural β-amyloid) may be more efficient at catalyzing hydrolysis due to a higher efficiency of binding the β-amyloid. Once bound, these antibodies force the protein into a transition state conformation for hydrolytic cleavage. Alternatively, antibodies which only minimally cross react with natural β-amyloid, although less efficient at binding native β-amyloid, are likely to be more efficient at forcing the bound β-amyloid into the transition state conformation for hydrolytic cleavage. It should be pointed out that failure to detect binding of the anti-transition state antibodies to natural β-amyloid by the ELISA methods presented in the Exemplification herein does not necessarily reflect an inability to bind natural β-amyloid sufficiently to function as a catalytic antibody. More likely, a lack of detection merely reflects the sensitivity limitations of the assay.

Antibodies which have substantial affinity for the predicted cleavage products of the native β-amyloid peptide may be subject to product inhibition and might therefore exhibit low turnover. Such undesirable antibodies can be identified by secondary screening using peptides which contain epitopes of the predicted cleavage products (e.g., via ELISA).

In a preferred embodiment, the antibodies are monoclonal. Monoclonal antibodies are produced by immunizing an animal (e.g., mouse, guinea pig, or rat) with the transition state analog antigen, and subsequently producing hybridomas from the animal, by standard procedures. Hybridomas which produce the desired monoclonal antibodies are identified by screening. One example of a screening method is presented in the Exemplification section which follows. In another embodiment, the antibodies are polyclonal. Polyclonal antibodies are generated by immunizing an animal (e.g., a rabbit, chicken, or goat) with antigen and obtaining sera from the animal. Polyclonal antibodies which have the desired binding specificities can be further purified from the sera by one of skill in the art through the course of routine experimentation.

Catalytic antibodies specific for β-amyloid can alternatively be generated in an individual through the use of anti-idiotype vaccines designed to elicit the production of catalytic antibodies. Such vaccines are described in the disclosure of Raso and Paulus (ANTI-IDIOTYPE VACCINES TO ELICIT CATALYTIC ANTIBODIES, U.S. Pat. No. 6,140,091 (2000)), the contents of which are incorporated herein by reference.

Another aspect of the present invention is the use of statine and reduced peptide bond analogs to elicit catalytic antibodies having proteolytic activity. The Exemplification section below details methods for using statine analogs as antigen in the production of catalytic antibodies, and also lists examples of anti-transition-state antibodies generated using these methods. The "statyl" moiety is derived from naturally evolved protease transition state inhibitors like amastatin, pepstatin, and bestatin. These naturally-occurring statine-based inhibitors have been used to effectively block the activity of aminopeptidases, aspartic proteases and the HIV protease. Synthetic peptides containing a statine residue offer novel features for the induction of catalytic antibodies. The statyl moiety has a tetrahedral bond geometry, its length is extended by two $CH_2$ units, it has a strategically placed OH group and the structure has no charge. The presence of the additional $CH_2$ units is expected to elicit a more elongated antibody combining site, and antibodies possessing this extended site will induce extra strain on the peptide substrate, producing an accelerated catalysis. In addition, the —OH group in these statine analogs is thought to better approximate the position and chemistry of the true transition state. Statine-based transition-state analogs should therefore elicit a class of antibodies which is significantly different from those obtained from the more commonly used negatively charged phosphonate analogs.

Reduced peptide bond analogs introduce a tetrahedral configuration, without increasing the distance between amino acid residues. This feature should more closely approximate the true transition state geometry, than previously used analogs. A positively charged secondary amine replaces the amide nitrogen of the natural polypeptide and should elicit a complementary negatively charged side chain at a proximal locus in the antibody combining site. The presence of such ancillary glutamyl or aspartyl groups on the antibody will assist antibody-mediated catalysis of peptide cleavage via acid-base exchange. Reduced peptide bond-based transition-state analogs should therefore elicit a class of antibodies which is significantly different from those obtained from using the more commonly used negatively charged phosphonate analogs. Reduced peptide bond analogs and statine analogs can be used to produce specific transition state analog antigens for a wide variety of proteins or polypeptides. These antigens can in turn be used to generate the respective catalytic antibodies.

Administration of the β-amyloid catalytic antibodies described above can be used in the methods described above for 1) sequestering free β-amyloid in the bloodstream of an animal, 2) reducing levels of β-amyloid in the brain of an animal, and 3) preventing the formation of amyloid plaques in the brain of an animal, to generate the analogous results. Experiments presented in the Exemplification demonstrate that immunization of an animal with a transition state analog results in the generation of an immune response to produce antibodies which recognize the transition state, and which catalyze hydrolysis of the β-amyloid protein. This indicates that the transition state analogs can be used as antigens in these methods to induce the production of antibodies in the animal which recognize and catalyze cleavage of endogenous β-amyloid.

Methods which involve reducing overall levels of β-amyloid in an animal through the proteolytic action of the above described catalytic antibodies are also encompassed by the present invention. The presence of functional catalytic antibodies in the circulation of an animal will reduce the level of intact β-amyloid in the circulation by selective hydrolytic cleavage. Accordingly, the present invention provides a method for reducing levels of circulating β-amyloid in an animal by introducing the above described catalytic antibodies into the animal. Administration of the antibodies to the animal is preferably via intravenous administration. Such antibodies are either monoclonal, mixed monoclonal, polyclonal or any mixture thereof. The origin of the antibody may affect the half-life of the antibody in the animal; antibodies from less related species are more likely to be recognized as foreign by the animal's immune system. Preferably, administered antibodies are derived from a species closely related to the animal, to maximize half-life and minimize adverse reactions by the host. Administration of isolated variable region antibody fragments may produce beneficial results in this regard.

The present invention also provides a method for reducing levels of circulating β-amyloid in an animal by immunizing the animal with a β-amyloid transition state analog to induce endogenous catalytic antibody production. The use and design of such vaccines is described above, and detailed in the Exemplification section below.

The reduction of β-amyloid levels in the circulation of an animal is expected to displace the equilibrium of β-amyloid in the body, and ultimately lead to a reduction in the levels of β-amyloid in the brain of the animal through mass action. In this respect, the present invention provides methods for reducing the levels of β-amyloid in the brain of an animal, by either administering catalytic antibodies to the animal, or by administering a transition state analog to induce endogenous antibody production. It follows that these procedures also have value as methods for preventing the formation of amyloid plaques in the brain of an animal, since the resulting reduction in the levels of β-amyloid in the brain of an animal should prevent the formation of amyloid plaques. These procedures also have value as methods for disaggregating amyloid plaques present in the brain of an animal, since evidence indicates that lower brain β-amyloid levels can lead to the disaggregation of plaques.

Another aspect of the present invention provides a more direct method of altering the distribution of β-amyloid in the brain by actually delivering anti-β-amyloid antibodies to the brain. Methods described above for reducing levels of β-amyloid in the brain and for preventing aggregation of amyloid plaques depend upon exchange between β-amyloid pools in the blood, tissues, cerebrospinal fluid and the brain, the exchange being driven by an antibody-mediated disruption of the equilibrium between these different pools. In contrast, delivery of anti-β-amyloid antibodies to the brain will directly affect β-amyloid aggregation. Evidence presented in the Exemplification section below indicates that the binding of certain anti-β-amyloid antibodies inhibits the initial aggregation of β-amyloid in vitro, and also disaggregates preformed in vitro β-amyloid complexes. Moreover, if insoluble peptide is in equilibrium with a low level of soluble β-amyloid, then an anti-β-amyloid binding antibody could upset this balance and gradually dissolve the precipitate. These observations indicate that the presence of β-amyloid antibodies in the brain will directly inhibit the formation of amyloid plaques and will also disaggregate preformed plaques by disrupting the dynamic equilibrium between soluble β-amyloid and fibrillar β-amyloid deposited as plaques. Furthermore, a highly active catalytic antibody is expected to destroy insoluble β-amyloid plaques by hydrolytically cleaving the constituent aggregated peptides.

One way of delivering antibodies to the brain is by producing vectorized antibodies competent for transcytosis across the blood-brain barrier. Vectorized antibodies are produced by covalently linking an antibody to an agent which promotes delivery from the circulation to a predetermined destination in the body. Examples of vectorized molecules which can traverse the blood-brain barrier are found in the prior art (Bickel et al., *Proc. Natl. Acad. Sci. USA* 90: 2618-2622 (1993); Broadwell et al., *Exp. Neurol.* 142: 47-65 (1996)). In these examples, antibodies are linked to another macromolecule, the antibodies being the agent which promotes delivery of the macromolecules. One example of such an agent is an antibody which is directed towards a cell surface component, such as a receptor, which is transported away from the cell surface. Examples of antibodies which confer the ability to trancytose the blood-brain barrier include, without limitation, anti-insulin receptor antibodies, and also anti-transferrin receptors (Saito et al., *Proc. Natl. Acad. Sci. USA* 92: 10227-31 (1995); Pardridge et al., *Pharm. Res.* 12: 807-816 (1995); Broadwell et al., *Exp. Neurol.* 142: 47-65 (1996)). This first antibody is covalently linked to an antibody which binds β-amyloid. Alternatively, coupling the β-amyloid antibodies to ligands which bind these receptors (e.g., insulin, transferrin, or low density lipoprotein) will also produce a vectorized antibody competent for delivery to the brain from the circulation (Descamps et al., *Am. J. Physiol.* 270: H1149-H1158 (1996); Duffy et al., *Brain Res.* 420: 32-38 (1987); Dehouck et al., *J. Cell Biol.* 138: 877-889 (1997)).

A vector moiety can be chemically attached to the anti-β-amyloid antibody to facilitate its delivery into the central nervous system. Alternatively, the moiety can be genetically engineered into the antibody as an integral component. This vector component can be for example, an anti-transferrin receptor antibody or anti-insulin receptor antibody which binds the receptors present on the brain capillary endothelial cells (Bickel et al., *Proc. Natl. Acad. Sci. USA* 90: 2618-22 (1993); Pardridge et al., *J. Pharmacol. Exp. Ther.* 259: 66-70 (1991); Saito et al., *Proc. Natl. Acad. Sci. USA* 92: 10227-31 (1995); Friden et al., *J. Pharm. Exper. Ther.* 278: 1491-1498 (1996)) which make up the blood-brain barrier. The resulting bifunctional antibody will attach to the appropriate receptors on the luminal side of the vessel (Raso et al., *J. Biol. Chem.* 272: 27623-27628 (1997); Raso et al., *J. Biol. Chem.* 272: 27618-27622 (1997); Raso, V. *Anal. Biochem.* 222: 297-304 (1994); Raso et al., *Cancer Res.* 41: 2073-2078 (1981); Raso et al., Monoclonal antibodies as cell targeted carriers of covalently and non-covalently attached toxins. In Receptor mediated targeting of drugs, vol. 82. G. Gregoriadis, G. Post, J. Senior and A. Trouet, editors. NATO Advanced Studies Inst., New York. 119-138 (1984)). Once bound to the receptor, both. components of the bispecific antibody pass across the blood-brain barrier by the process of transcytosis. Anti-β-amyloid antibodies which have entered the brain interact directly with both β-amyloid plaques and the soluble β-amyloid pool. It has been estimated that concentrations of macromolecules in the $10^{-8}$-$10^{-7}$M range can be achieved in the brain using vector-mediated delivery via these brain capillary enriched protein target sites (Maness et al., *Life Sciences* 55: 1643-1650 (1994); Lerner et al., *Science* 252: 659-667 (1991)). Importantly, the vector appears safe since animals dosed daily for two weeks with an anti-transferrin receptor antibody displayed no loss of integrity of the blood-brain barrier, using a radioactive sucrose probe (Broadwell et al., *Exp. Neurol.* 142: 47-65 (1996)).

The Exemplification details the production of vectorized bispecific antibodies which bind β-amyloid. The bispecific antibodies transcytose across the blood brain barrier via a first specificity which binds the transferrin receptor. Use of antibodies which bind the transferrin receptor for delivery of agents across the blood brain barrier is described by Friden et al. in U.S. Pat. Nos. 5,182,107; 5,154,924; 5,833,988; and 5,527,527; the contents of which are incorporated herein by reference.

Results from experiments presented in the Exemplification section which follows indicate that the produced bispecific antibodies retain their separate specificities and are delivered across the blood-brain barrier into the brain parenchyma and brain capillaries of a live animal when administered intravenously.

Alternate methods for the production of bispecific antibodies have been described for genetically engineering bispecific reagents or for producing them intracellularly by fusing the two different hybridoma clones (Holliger et al., *Proc. Natl. Acad. Sci.* 90: 6444-6448 (1993); Milstein et al., *Nature* 305: 537 (1983); Mallander et al., *J. Biol. Chem.* 269: 199-206 (1994)). Vectorized bispecific antibodies produced by these techniques can also be used in the methods of the present invention.

Since the introduction of whole antibodies into the brain might be detrimental if they were to fix complement and promote complement-mediated lysis of neuronal cells, it may be beneficial to produce and utilize smaller vectorized F(ab')$_2$ bispecific reagents. It has been shown that aggregated β-amyloid itself can fix complement in the absence of any antibody and that the resulting inflammation may contribute to the pathology of Alzheimer's disease. The possibility of intracerebral antibody having a similar effect can be greatly reduced by eliminating the Fc region of the antibody. Moreover, since coupling of Fab' halves uses the intrinsic hinge region cysteines, no extraneous substituent linkage groups need be added. Faster or more efficient entry into the brain represents another potential advantage that smaller F(ab')$_2$ or Fv$_2$ reagents may provide for intracerebral delivery. In addition, the two types of vectorized molecules may have different biodistribution and plasma half-life characteristics (Spiegelberg et al., *J. Exp. Med.* 121: 323 (1965)).

Depending on their design, anti-β-amyloid bispecific antibodies in the brain can reduce soluble β-amyloid and β-amyloid deposits by three potential mechanisms. An anti-β-amyloid bispecific antibody that tightly binds soluble β-amyloid will not only sequester the peptide but, due to efflux of vectorized molecules from the central nervous system (Kang et al., *J. Pharm. Exp. Ther.* 269: 344-350 (1994)), may also carry the bound β-amyloid out of the brain, releasing it into the blood stream. Such a clearance mechanism would lead to a continuous cycling of β-amyloid out of the brain. In addition, if the antibodies have catalytic activity, they will directly reduce the levels of harmful β-amyloid by degradation. Since catalytic antibodies exhibit turnover, each antibody can inactivate many β-amyloid molecules. Thus much less vectorized bispecific antibody has to be delivered into the brain to achieve the desired depletion of β-amyloid.

To be effective the anti-β-amyloid sites of a bispecific antibody must be empty before passage out of the blood and into the brain. Therefore the concentration of bispecific antibody in animals must exceed the level of β-amyloid circulating in the blood. Calculations performed based upon known β-amyloid levels (Scheuner et al., *Nature Med.* 2: 864-870 (1996)) and a medium-range plasma level of bispecific antibody expected in a treated animal indicated 99.9% of the bispecific antibodies that enter the brain will have unoccupied anti-β-amyloid combining sites.

Another way of delivering antibodies to the brain is via direct infusion of anti-β-amyloid antibodies into the brain of an animal. This technique gives these antibodies immediate access to β-amyloid in the brain without having to cross the blood-brain barrier. Direct infusion can be accomplished via direct parenchymal or intracerebroventricular infusion (Knopf et al., *J. Immunol.* 161: 692-701 (1998)). Briefly, the animal is anesthetized and placed in a stereotaxic frame. A midsagittal incision is made on the scalp to expose the skull and the underlying fascia is scraped away. A hole is drilled to accept a sterilized length of stainless steel hypodermic tubing, which is stereotaxically advanced so that its tip is appropriately located in the brain. A guide cannula is then attached to the skull and sealed. The cannula remains in place for multiple infusions of antibody into the brain. A bolus of a sterile 50 mg/ml solution of a monoclonal anti-β-amyloid can be infused over a 2-8 minute period into an immobilized animal via an injection cannula.

Delivery of catalytic antibodies into the brain of an animal via one of the above described methods, can also be used to disaggregate amyloid plaques present in the brain. The advantage of delivering an β-amyloid-specific catalytic antibody into the brain is two-fold. The β-amyloid peptide is permanently destroyed by such antibodies and, since catalysis is continuous, each antibody inactivates many target β-amyloid molecules in the brain. Thus much less antibody has to be infused into the central nervous system to achieve the desired depletion of β-amyloid.

The amount of antibody to be administered or delivered to the animal should be sufficient to cause a significant reduction in β-amyloid levels in the brain of the animal. The appropriate amount will depend upon various parameters (e.g., the particular antibody used, the size and metabolism of the animal, and the levels of endogenous β-amyloid) and is to be determined on a case by case basis. Such determination is within the means of one of average skill in the art through no more than routine experimentation.

It is expected that additional benefits with respect to lowering brain β-amyloid levels and preventing or disaggregating amyloid plaques can be achieved through utilizing a combination of one or more of the above described approaches.

EXEMPLIFICATION

Section 1: Retention of β-amyloid in the Circulation

Synthesis of β-amyloid Peptide Antigens

The amino acid sequence of the 43 residue β-amyloid peptide (Aβ) is listed in FIG. 1. To determine which sites on this Aβ peptide were best suited for antibody-mediated therapy, three key regions (amino-terminal, central and carboxy-terminal) of the Aβ 43-mer were chosen to generate epitope-specific vaccines. These shortened peptides served as antigenic epitopes to induce a highly specific antibody response.

Monoclonal antibodies to the amino-terminal region of Aβ have been shown in the past to have the ability to solubilize Aβ aggregates (Solomon et al., *Proc. Natl. Acad. Sci. USA* 94(8): 4109 (1997); Solomon et al., *Proc. Natl. Acad. Sci. USA* 93(1): 452 (1996)). A peptide consisting of the amino-terminal region of Aβ was similarly designed for the present experiments (shown in FIG. 2 and listed in SEQ ID NO: 2) and used to elicit amino-terminal specific antibodies that bind Aβ. A Cys residue was added to the C-terminus of the Aβ sequence to provide a suitable linkage group for coupling this peptide to an antigenic carrier protein such as maleimide-activated Keyhole Limpet Hemocyanin (KLH).

A peptide encompassing the central region of Aβ was also synthesized (shown in FIG. 3 and listed in SEQ ID NO: 3). A Cys residue was placed at the N-terminus of the Aβ sequence to provide a sulfhydryl linkage group for coupling the peptide to antigenic carrier proteins such as maleimide-activated KLH.

To produce an antigen for eliciting an immune response directed against the carboxy-terminus of Aβ (Suzuki et al., *Science* 264: 1336 (1994)), a decapeptide encompassing the N-terminal region of Aβ, with an additional Cys residue at the N-terminus, was synthesized (Shown in FIG. 4, and listed in SEQ ID NO: 4). The Cys substitution was designed to provide a sulfhydryl linkage group for coupling the peptide to antigenic carrier proteins such as KLH.

Coupling the Peptides to an Antigenic Carrier Protein

The different Cys containing Aβ peptides were individually thioether-linked to maleimide-activated KLH. A multivalent Aβ vaccine was also produced by simultaneously linking all three of these peptides to maleimide-activated KLH. In addition the full-length Aβ 43-mer was linked to KLH using glutaraldehyde.

Antibodies Elicited with the β-amyloid Vaccines

Normal BALB/c mice were immunized by standard procedures with the KLH-linked Aβ vaccines described above. The mice were either bled or sacrificed for removal of the spleen for hybridoma production. Sera and monoclonal antibodies obtained were characterized for binding to Aβ.

Table 1 shows the results from an ELISA run with 1/100 diluted serum from two non-immunized control mice versus 1/100 and 1/1000 diluted serum from a mouse that was immunized with a central region Aβ peptide-KLH vaccine. The free Aβ peptide was adsorbed directly onto the microtitre plate to avoid detection of anti-KLH antibodies in the serum.

TABLE 1

ELISA for Binding to the Central Region Aβ Peptide

| Addition | | Antibody Bound (O.D. 450 nm) |
|---|---|---|
| Control Serum A | 1/100 | 0.666 |
| Control Serum B | 1/100 | 0.527 |
| Mouse 1 antiserum | 1/100 | 3.465 |
| Mouse 1 antiserum | 1/1000 | 2.764 |

Monoclonal antibodies raised against this central region Aβ peptide and produced by hybridoma fusion were identified using the above described ELISA assay. A binding assay was performed to determine whether the monoclonal anti-Aβ antibodies identified also bound to the full length Aβ peptides. $^{125}$I-Aβ$_{1-43}$ probe was incubated with hybridoma secretions from the indicated clones. A standard polyethylene glycol separation method was used to detect $^{125}$I-Aβ$_{1-43}$ bound antibody (Table 2). Results presented in Table 2 indicate that the antibodies generated to the peptide fragments also bound full length Aβ$_{1-43}$.

TABLE 2

$^{125}$I-Aβ$_{1-43}$ Binding Assay

| Addition | | $^{125}$I-Aβ$_{1-43}$ Bound (cpm) |
|---|---|---|
| Control | Hy | 3,171 |
| Control | Hy | 2,903 |
| 6E2 | | 15,938 |
| 6E2 | 1/10 | 9,379 |
| 3B1 | | 12,078 |
| 3B1 | 1/10 | 3,353 |
| 8E3 | | 10,789 |
| 8E3 | 1/10 | 3,249 |

It was reported that when $^{125}$I-Aβ$_{1-40}$ is added to human plasma, ~89% binds to albumin (Biere et al., *J. of Biol. Chem.* 271(51): 32916 (1996)). This raises the concern that the bound albumin will interfere with antibody binding. Binding assays were performed in the presence and absence of serum albumin, to determine whether albumin binding interferes with antibody binding to Aβ. The ability of purified 5A11 monoclonal anti-Aβ antibody to bind $^{125}$I-Aβ$_{1-40}$ was unaffected by the presence of human serum albumin (HSA) at 60 mg/ml, even though this was a 500-fold molar excess over the antibody concentration (Table 3). These results indicate that the ability of antibodies to bind to and sequester Aβ in the blood will not be attenuated by the presence of other binding proteins.

TABLE 3

$^{125}$I-Aβ$_{1-40}$ Binding to Antibody in the Presence of Human Serum Albumin*

| Addition | $^{125}$I-Aβ$_{1-40}$ Bound (cpm) | Specifically Bound (% of total added) |
|---|---|---|
| Control | 8,560 | — |
| +5A11 anti-Aβ | 64,589 | 79 |

TABLE 3-continued $^{125}$I-Aβ$_{1-40}$ Binding to Antibody in the Presence of Human Serum Albumin*

| Addition | $^{125}$I-Aβ$_{1-40}$ Bound (cpm) | Specifically Bound (% of total added) |
|---|---|---|
| Control + HSA* | 3,102 | — |
| +5A11 anti-Aβ + HSA* | 55,304 | 75 |

*HSA at 60 mg/ml (~1 mM); anti-Aβ 5A11 at 2 × 10$^{-6}$ M; Added ~70,000 cpm of $^{125}$I-Aβ$_{1-40}$ Monoclonal Antibody Production A mouse was immunized with a KLH conjugate of the central region Aβ$_{10-25}$ peptide (This peptide antigen had incorporated phenylalanine statine transition state analogs, discussed further in Section II, below). A hybridoma fusion was performed and the resulting monoclonal antibodies analyzed to characterize the specificity of the immune response to the vaccine. Hybridoma supernatants produced in the fusion were screened using ELISA to assess their binding to the Aβ$_{1-43}$ peptide.

The monoclonal antibodies produced were determined to bind to the Aβ$_{1-43}$ peptide adsorbed directly onto an ELISA plate. Strong color reactions were obtained in this ELISA using only 10 μl of hybridoma supernatant while the addition of media alone produced low background color. These results indicate that the antibodies not only bound to the small peptide immunogen but they were also reactive with the full-length Aβ$_{1-43}$. Importantly, antibodies bound to the carrier-free Aβ peptide adsorbed directly onto microtitre plates, showing their specificity for the peptide rather than the immunogenic carrier. The high affinity 5A11 monoclonal antibody (Table 3) was obtained from this hybridoma fusion.

A second mouse was immunized with a KLH conjugate of the Aβ$_{35-43}$ analog encompassing the C-terminal region of Aβ. Serum from the mouse was screened for reaction with Aβ$_{1-43}$ adsorbed directly onto the ELISA wells. The assay results are presented in Table 4. The spleen of this mouse was then used for a hybridoma fusion to further characterize the specificity of its immune response. Importantly, none of the mice immunized with Aβ vaccines or the anti-Aβ ascites-producing mice displayed ill effects even though some of those induced antibodies cross-react with mouse Aβ and mouse amyloid precursor protein.

TABLE 4

ELISA for Binding of Antiserum Directed to the Carboxy-terminal Aβ Peptide

| Addition | Antibody Bound (O.D. 450 nm) Native Aβ$_{1-43}$ |
|---|---|
| Control Serum | 0.484 |
| Mouse Antiserum | 1.765 |

Monoclonal antibodies from hybridoma clones generated above were screened for binding to the small carboxy-terminal peptide Aβ$_{35-43}$ and the full-length Aβ$_{1-43}$. Results are presented in FIG. 5. The monoclonal antibodies bound to the carboxy-terminal locus on each of these carrier-free Aβ peptides adsorbed directly to the microtitre plate, confirming their specificity for the peptide rather than the immunogenic carrier. The clones were also tested with Aβ$_{1-40}$ to identify antibodies which do not react with this shortened, 40 amino acid residue version of Aβ and thus will specifically bind to the carboxy-terminus of $A\beta_{1-43}$ (FIG. 5). Used therapeutically, this vaccine should elicit antibodies which will preferentially bind the less abundant, but more noxious $A\beta_{1-43}$ species in the blood as opposed to the smaller and less detrimental $A\beta_{1-40}$.

In a separate experiment, mice were immunized with a vaccine comprised of a cocktail of the three distinct KLH-peptide antigens (FIGS. 2-4) representing the distinct regions of β-amyloid (FIG. 1). Control mice were immunized with KLH alone. The antigens were emulsified in complete Freunds adjuvant prior to the first injection and in incomplete Freunds adjuvant for subsequent injections. Tests were performed on diluted serum from these Aβ-KLH immunized mice to determine the presence of specific anti-Aβ antibodies. The $A\beta_{1-16}$, $A\beta_{14-25}$, $A\beta_{34-43}$, $A\beta_{1-40}$ and $A\beta_{1-43}$ peptides were used to identify antibody specificity. The peptides were adsorbed directly onto an ELISA plate. The results are presented in Table 5. The results indicate that mice immunized with the cocktail of the three peptide antigens produced serum containing antibodies which react with the amino-terminal, central region, and carboxyl-terminal peptides, as well as with the full-length Aβ 40-mer and 43-mer. The constant presence of this spectrum of anti-Aβ antibodies will be very effective in binding all of the soluble Aβ in the peripheral circulation of a vaccinated animal.

TABLE 5

ELISA to Measure the Serum Antibodies Present in Immunized Mice

| Immunogen | ELISA READING (O.D. 450 nm) | | | | |
|---|---|---|---|---|---|
| | $A\beta_{1-16}$ | $A\beta_{14-25}$ | $A\beta_{34-43}$ | $A\beta_{1-40}$ | $A\beta_{1-43}$ |
| Mouse 1 (Control) KLH | 0.076 | 0.038 | 0.064 | 0.042 | 0.066 |
| Mouse 2 Aβ-KLH Cocktail | 3.013 | 1.258 | 3.191 | 2.337 | 2.598 |
| Mouse 3 Aβ-KLH Cocktail | 1.484 | 1.180 | 2.068 | 1.758 | 1.680 |
| Mouse 4 Aβ-KLH Cocktail | 1.486 | 1.072 | 2.276 | 1.444 | 1.709 |

Vaccine Trials in Non-Human Primates

Given the potential importance of β-amyloid vaccine therapy for human patients of Alzheimer's disease, a human-compatible, alum-based Aβ peptide vaccine preparation has been tested in non-human primates. Antibody production and safety studies for the human-compatible β-amyloid vaccines have commenced in Cynomolgus monkeys (*Macaca fascicularis*). This animal system is highly relevant to human applications since the predicted amino acid sequence of β-amyloid in these primates is identical to humans, and their basic physiology and immunological systems closely approximate those which will be encountered in a clinical situation. Cynomolgus monkeys were vaccinated monthly and were periodically bled to monitor anti-Aβ levels in the serum. The monkeys were also observed for any ill effects.

The Cynomolgus monkeys mounted a strong immune response to a single injection of the simplest vaccine preparation composed of the full length β-amyloid peptide adsorbed to an aluminum hydroxide gel. The specificity of those early anti-β-amyloid antibodies was characterized by ELISA using various Aβ peptide fragments (Table 6). This analysis indicated that the monkeys produced antibodies that bind to the full-length peptide and react with its amino-terminal, central and carboxyl-terminal regions.

TABLE 6

ELISA to Measure the Serum Antibodies Present in Aβ Vaccinated *Macaca fascicularis*

| Vaccination Schedule | ELISA READING (O.D. 450 nm) | | | | |
|---|---|---|---|---|---|
| | $A\beta_{1-16}$ | $A\beta_{14-25}$ | $A\beta_{34-43}$ | $A\beta_{1-40}$ | $A\beta_{1-43}$ |
| Pre-Vaccination | 0.511 | 0.404 | 0.370 | 0.380 | 0.235 |
| Aβ/Alum (1st month) | 2.115 | 1.687 | 0.671 | 2.393 | 2.479 |

Importantly, the vaccinated monkeys are perfectly healthy and appear compatible with the anti-Aβ antibodies that have been circulating in their body for over three months. Thus far, there are no apparent side effects due to cross-reaction of the anti-Aβ antibodies with naturally occurring β-amyloid precursor protein or other vital components. These animals were closely observed by a veterinarian, and have exhibited no signs of autoimmune disease, immune complex disease or any other adverse/toxic reaction to the vaccination.

In continuing experiments boost injections will be performed as per usual methods. The sera produced will be monitored for antibody specificity and affinity parameters as the immune response intensifies and matures. At termination, a complete necropsy and histopathological examination will be performed on the monkeys. Genetically engineered Aβ vaccines, discussed below, will also be evaluated in the Cynomolgus monkeys to determine if they will prove to be even better immunogens.

Antibodies Affect the Distribution of $^{125}$I-Aβ in Normal Mice

Anti-Aβ antibodies in the circulation cannot cross the blood-brain barrier to a significant extent and therefore should act as a sink that prevents $^{125}$I-$A\beta_{1-40}$ from reaching the brain. This retention effect was demonstrated by measuring the blood levels in mice 4 h after injecting them with equal amounts of $^{125}$I-$A\beta_{1-40}$ either alone or along with our 5A11 anti-Aβ monoclonal antibody (Table 7). The passage of $^{125}$I-$A\beta_{1-40}$ out of the peripheral circulation was greatly curtailed in animals which concomitantly received the specific anti-Aβ antibody. That finding extends the in vitro results obtained with the 5A11 antibody (Table 3) by demonstrating the antibody can effectively bind Aβ in an experimental animal. The observation that animals treated with this antibody retained 10-times more $^{125}$I-$A\beta_{1-40}$ in the circulation indicates that the equilibrium distribution of Aβ in the body can be dramatically altered by selective sequestration in the blood.

TABLE 7

Anti-Aβ Antibody Impedes the Passage of $^{125}$I-$A\beta_{1-40}$ Out of the Circulation

| Mouse Injected With; | $^{125}$I-$A\beta_{1-40}$ in Blood (cpm/gm) |
|---|---|
| $^{125}$I-$A\beta_{1-40}$ alone | 27,300 |
| $^{125}$I-$A\beta_{1-40}$ + 5A11 anti-Aβ | 278,900 |

Genetically Engineered Vaccines

Genetically engineered β-amyloid antigen vaccines for use in humans are currently being developed in order to induce protective levels of anti-β-amyloid antibodies. β-amyloid fragments will be engineered into chimeric Aβ vaccines which incorporate highly immunogenic carrier moieties to increase the appropriate antigenic response in a human patient. Carrier moieties suitable for use include diphtheria toxoid (DT) and the hepatitis B core antigen (HBcAg). These represent powerful delivery systems for β-amyloid peptides, and are known to induce an excellent, high titer immune response when used with alum as an adjuvant.

DT is licensed for use as a conjugate vaccine for *H. influenzae* type B and renders this immunogen T-cell dependent. The expression of DT in recombinant *E. coli* is high. One or more of the above described β-amyloid peptides will be fused at the C-terminus of the catalytic domain of DT, or at either end of the combined transmembrane/receptor binding domains of DT. The produced fusions will be used with an aluminum hydroxide gel adjuvant to generate potent vaccines.

High titers of antibody directed against heterologous epitopes have been produced using the HBcAg delivery systems and aluminum hydroxide gel adjuvant. HBcAg has several distinct advantages as a fusion partner for Aβ peptides. The immunodominant internal site between amino acids 75 and 81 can accommodate heterologous sequences up to 45 amino acids. The core self-assembles into larger 27 nm particles that are highly immunogenic. Furthermore, HBcAg can be produced in recombinant *E. coli* at elevated levels.

The genetically engineered vaccines produced will be tested for effectiveness in depleting or preventing plaques using mouse and other relevant animal models. Antibody production and safety trials for the vaccines will be conducted in Cynomolgus monkeys.

Methods of the Invention

Peptide Synthesis. The 40 mer $A\beta_{1-40}$, the 43 mer $A\beta_{1-43}$, and the three small Aβ peptides $A\beta_{1-16}$, $A\beta_{10-25}$, and $A\beta_{35-43}$, were synthesized by standard automated Fmoc chemistry. Newly synthesized peptides were purified by HPLC and their composition was verified by mass spectral and amino acid analysis. The Aβ 43 mer was obtained from a commercial source (Bachem, Torrance, Calif.).

Conjugation of β-amyloid Peptides to Immunogenic Carriers. The small Aβ peptides were linked to the KLH carrier protein in order to render them antigenic. A Cys residue was strategically placed at the N- or C-terminal end of these Aβ peptides to provide a suitable linkage group for coupling them via a thioether bond to maleimide activated carrier proteins. This linkage is stable and attaches the peptide in a defined orientation. Addition of 20 peptides/KLH is typically obtained by this conjugation method. The longer, full length Aβ peptides were linked to carrier proteins using a glutaraldehyde coupling procedure.

β-amyloid Antigen Cocktail. The three Aβ peptides shown in FIGS. 2-4 were each individually conjugated to KLH. 20 μg of each of these three conjugates was then mixed together. This mixture was emulsified with complete Freunds adjuvant and injected i.p. into mice. Subsequent monthly i.p. booster injections used the same cocktail mixture emulsified in incomplete Freunds adjuvant. Control mice received a similar immunization protocol but using KLH which had not been conjugated with the Aβ peptides.

Immunization of Mice. Normal BALB/c mice were immunized by standard procedures with the KLH-linked Aβ vaccines described above. Briefly, mice were injected i.p. with antigen emulsified in complete Freunds adjuvant, followed by a second course in incomplete Freunds adjuvant. The mice were i.v. boosted with antigen in PBS three days prior to bleeding them or removing the spleen for hybridoma fusions to produce monoclonal antibodies.

None of the mice immunized with Aβ vaccines or the anti-Aβ ascites-producing mice displayed ill effects even though some of the antibodies cross-reacted with mouse Aβ and mouse amyloid precursor protein.

ELISA. The presence of bound anti-peptide antibodies was revealed by using a peroxidase-labeled anti-mouse IgG probe followed by the chromogenic substrate (Engvall et al., *Immunochemistry* 8: 871-875 (1971)).

Binding Assay. Both $A\beta_{1-43}$ and $A\beta_{1-40}$ were radiolabeled with $^{125}I$. The iodinated peptide was separated from unlabeled material by HPLC to give essentially quantitative specific activity (~2000 Ci/mmol) (Maggio et al., *Proc. Natl. Acad. Sci.* 89: 5462 (1992)). $^{125}I\text{-}A\beta_{1-43}$ probe was incubated for 1 h at 23° C. with Hy media taken from hybridoma clones producing monoclonal anti-Aβ antibodies. A standard polyethylene glycol separation method was used to detect the amount of $^{125}I\text{-}A\beta_{1-43}$ bound to antibody.

β-amyloid Vaccines for Primates. The immunogen used was a synthetic Aβ peptide encompassing amino acids 1-41 of the Aβ protein. This peptide was purified by HPLC and freeze-dryed and then resuspended in sterile water at a concentration of 1.5 mg/ml. The vaccine was prepared by mixing 7.5 ml of a 2% aluminum hydroxide gel adjuvant (Alhydrogel, Superfos Biosector, Denmark), referred to herein as alum gel, with 7.5 ml of the peptide. Tests showed that all of the peptide was adsorbed to the alum gel after mixing for 12 hours at 25° C.

Monkeys were initially vaccinated by intramuscular (i.m.) injection of 0.5 ml of the alum-adsorbed peptide. A second vaccination (boost) of the same vaccine preparation (0.5 ml) was administered a month later. Subsequent identical monthly injections (boosts) will be given until the experiment is terminated.

Genetically Engineered Vaccines. Highly immunogenic carrier moieties will be used to construct chimeric Aβ vaccines. Moieties used will include diphtheria toxoid (DT) and the hepatitis B core antigen (HBcAg). The HBcAg expression system will be utilized (Schodel et al., *Infect. and Immun.* 57: 1347-1350 (1989); Schodel et al., *J. of Exper. Med.* 180: 1037-1046 (1994); Schodel et al., *J. of Virology* 66: 106-114 (1992); Milich et al., *Annals New York Academy of Sciences:* 187-201 (1993)). The amino terminal end of the catalytic domain of HBcAg has a signal sequence which should allow the Aβ fusion protein to be secreted into the culture medium. The culture medium will be concentrated using a large Amicon ultrafiltration device, and the concentrate then chromatographed on a large Superdex 75 column. Recombinant products obtained from within lysed cells will be separated from bacterial protein using a combination of anion exchange and size exclusion FPLC.

Section II: Eliciting Monoclonal Antibodies with Transition State Antigens

Transition State Peptide Antigens

Different types of transition state peptide antigens were synthesized to use in the generation of antibodies which preferentially recognize (hydrolysis) transition states of Aβ at a predetermined amide linkage position.

A series of statine (Sta) transition state analogs encompassing the carboxy-terminal region of Aβ (Cys-Met-Val-Gly-Gly-Val/Sta-Val/Sta-Ile/Sta-Ala-Thr) were synthesized. Replacement of the proposed scissile peptide linkage between $Val_{39}$ and $Val_{40}$, $Val_{40}$ and $Ile_{41}$, and $Ile_{41}$ and $Ala_{42}$, with a "statyl" moiety (—CHOH—$CH_2$—CO—NH—) was designed to elicit catalytic antibodies that hydrolytically cleave Aβ at one of these sites (FIG. 6). Peptide synthesis was designed so as to generate the modifications at one of three, two of three, or three of the three possible positions, generating a mixture of seven differently modified peptides. A Cys residue was placed at the N-terminal position of these peptides to provide a suitable linkage group for coupling to a maleimide-activated carrier protein.

A series of phenylalanine statine (PhSta) transition state analogs encompassing the central region of Aβ (Cys-Tyr-Glu-Val-His-His-Gln-Lys-Leu-Val-Phe/PhSta-Phe/PhSta-Ala-Glu-Asp-Val-Gly-amide) was synthesized in this laboratory. Peptide synthesis was designed so as to generate the modifications at one of two or two of two of the two possible positions, generating a mixture of three differently modified peptides.

Replacement of the proposed scissile peptide linkage between Phe$_{19}$ and Phe$_{20}$, and between Phe$_{20}$ and Ala$_{21}$, with a statyl moiety (—CHOH—CH$_2$—CO—NH—) was designed to elicit catalytic antibodies that hydrolytically cleave Aβ at these sites (FIG. 7). A Cys residue was placed at the C-terminus of these peptides to provide a sulfhydryl linkage group for coupling the peptides to antigenic, maleimide-activated carrier proteins such as KLH.

Figure 8:
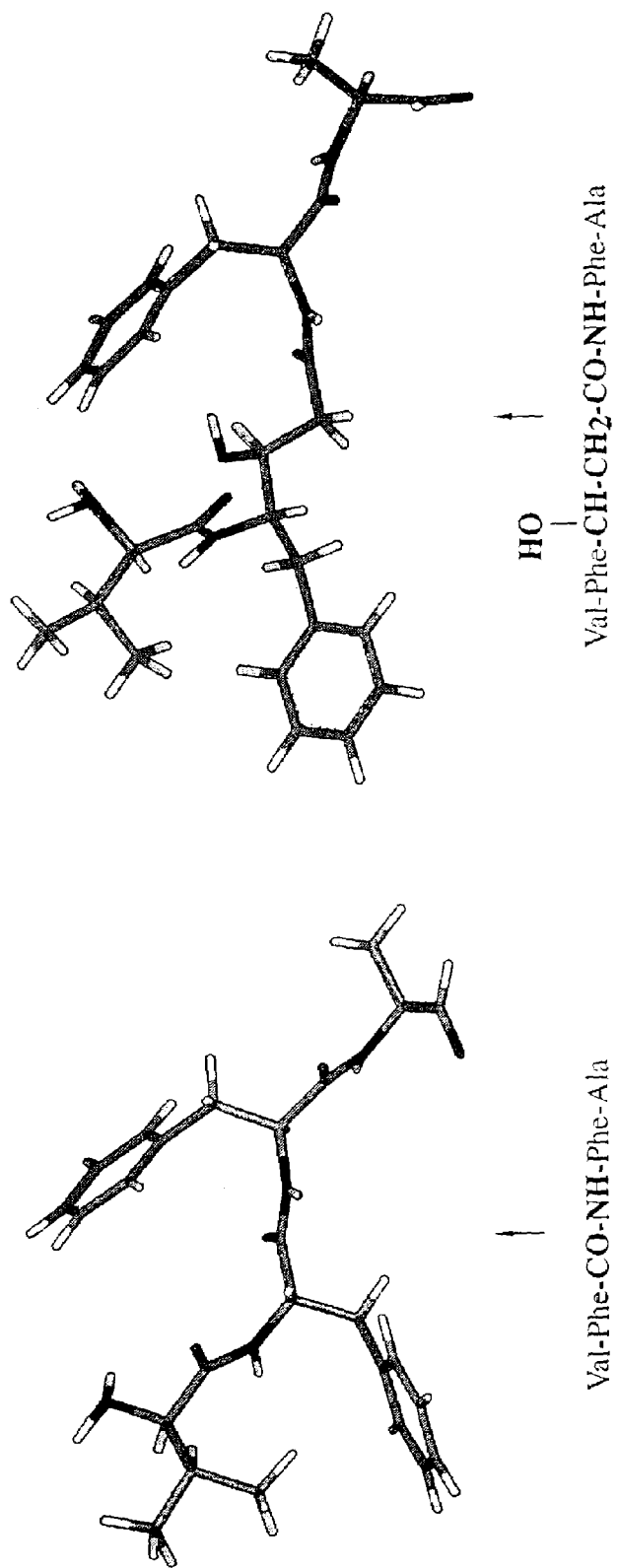
FIG. 8 is a structural comparison between the native β-amyloid peptide and the transition state phenylalanine statine β-amyloid peptide analog.

A structural comparison (FIG. 8) was made between the native Aβ peptide and the transition state phenylalanine statine Aβ peptide using a graphics workstation. An energy minimization algorithm (2000 iterations) was applied to arrange each peptide in its most favorable conformation.

The peptide link (—CO—NH—) between Phe$_{19}$ and Phe$_{20}$ was replaced with an elongated "statyl" moiety (—CHOH—CH$_2$—CO—NH—) and an energy minimization was applied. This orientation shows the difference between the planar peptide link (—CO—NH—) of natural Aβ (left) versus the extended, tetrahedral "statyl" moiety (—CHOH—CH$_2$—CO—NH—) in the transition state peptide (right).

An antibody combining site complementary to a tetrahedral statine transition state analog will force the planar peptide bond of the Aβ substrate into a transition state-like conformation. Such distortion should catalyze the cleavage of Aβ at that locus in the peptide sequence.

The possibility of using a reduced peptide bond linkage to mimic the transition state during hydrolysis of an amide linkage was also explored. A reduced peptide bond linkage can be easily placed at almost any site in the Aβ molecule to produce a reduced peptide bond transition state analog. This analog can also be used to elicit catalytic antibodies that will hydrolytically cleave Aβ at the chosen site. The reduced peptide bond transition state Aβ analog made was the (Gln-Lys-Leu-Val-Phe-CH$_2$—NH$_2^+$-Phe-Ala-Glu-Asp-Val-Gly-Cys-amide) central region peptide; [calculated 1,342 (M+1); observed 1,344].

Figure 9:
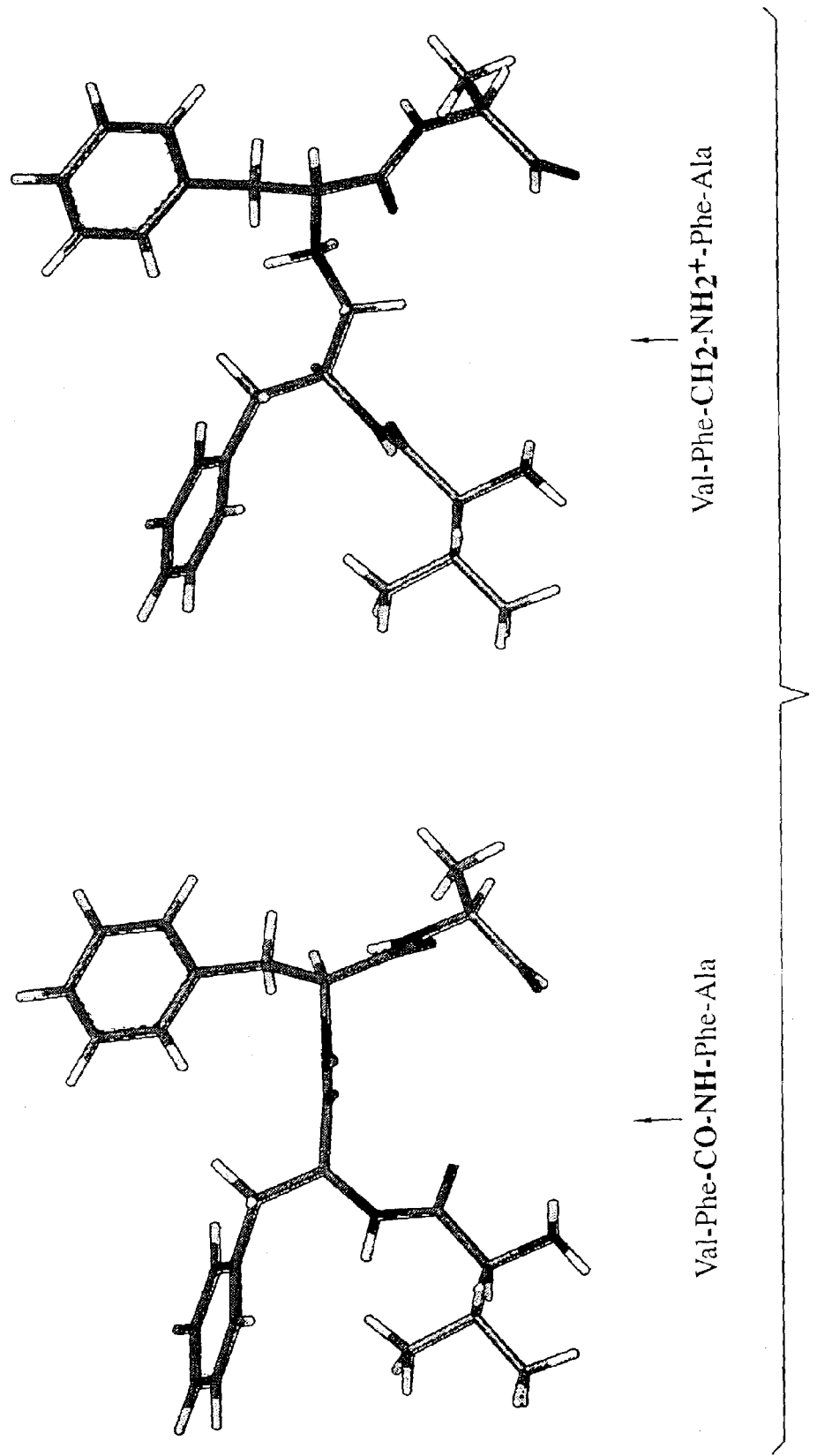
FIG. 9 is a structural comparison between the native β-amyloid peptide and the reduced peptide bond transition state β-amyloid peptide analog.

A structural comparison (FIG. 9) was made between the native Aβ peptide and the reduced peptide bond transition state Aβ analog using a graphics workstation. The peptide link (—CO—NH—) between Phe$_{19}$ and Phe$_{20}$ was replaced with a reduced peptide bond (—CH$_2$—NH$_2^+$—) and an energy minimization was applied. The orientation shown indicates the difference between the planar peptide link (—CO—NH—) of natural Aβ (left) versus the corresponding tetrahedral moiety (—CH$_2$—NH$_2^+$—) in the reduced peptide bond transition state analog (right). An energy minimization algorithm (2000 iterations) was applied to arrange each peptide in its most favorable conformation.

Figure 11:
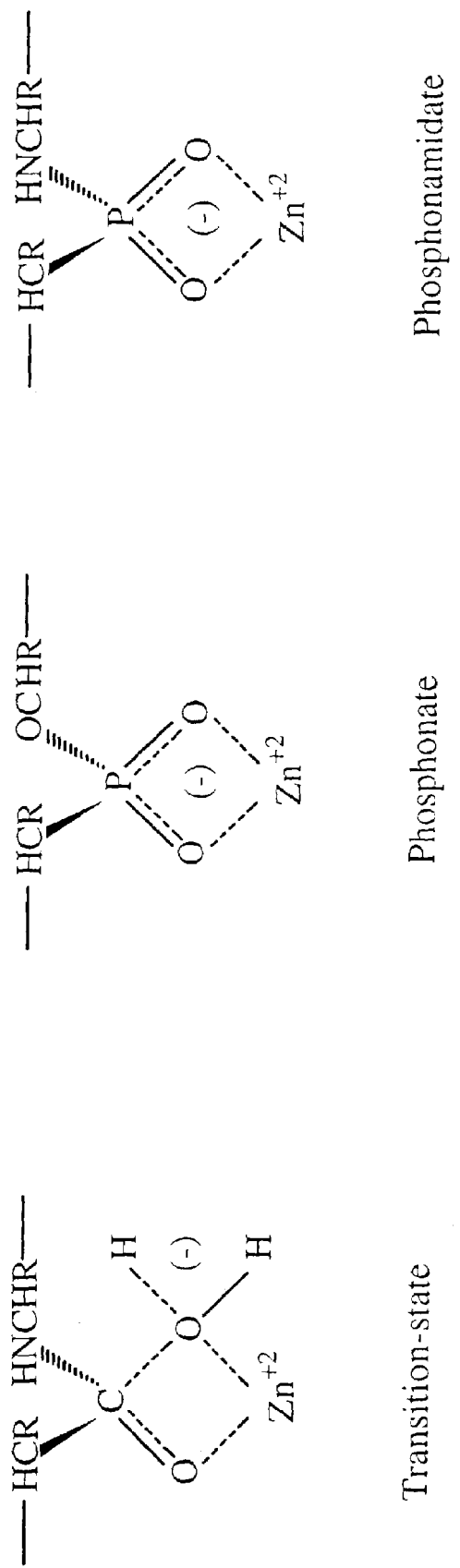
FIG. 11 indicates the putative transition state for peptide hydrolysis by zinc peptidases, compared to the phosphonate and phosphonamidate mimics.

A phosphonamidate transition state analog of the carboxy-terminal region of Aβ has also been synthesized (FIG. 10). Replacement of the proposed scissile peptide linkage between Gly$_{38}$ and Val$_{39}$ with a phosphonamidate moiety (—PO$_2^-$—NH—) was designed to elicit catalytic antibodies that will hydrolytically cleave Aβ at this site. The N-acetyl-Cys residue was placed at the position of Leu$_{34}$ to provide a suitable linkage group for coupling this peptide to an antigenic carrier protein. The structures in FIG. 11 represent the putative transition state for peptide hydrolysis by zinc peptidases, versus structure of and the phosphonate and phosphonamidate mimics. Similar tetrahedral transition state intermediates are known to be formed by reaction with each of the four classes of proteolytic enzymes, the serine-, cysteine-, aspartic- and metallo-peptidases.

A structural comparison was made between the native Aβ peptide and the transition state phosphonamidate Aβ peptide (FIG. 12) using a graphics workstation. The peptide link (—CO—NH—) between Gly$_{38}$ and Val$_{39}$ was replaced with a phosphonamidate bond (—PO$_2^-$—NH—) and an energy minimization was applied. The orientation shown in FIG. 12 illustrates the difference between the planar peptide link (—CO—NH—) of native Aβ (left) versus the corresponding tetrahedral phosphonamidate bond (—PO$_2^-$—NH—) in the transition state peptide (right).

Figure 12:
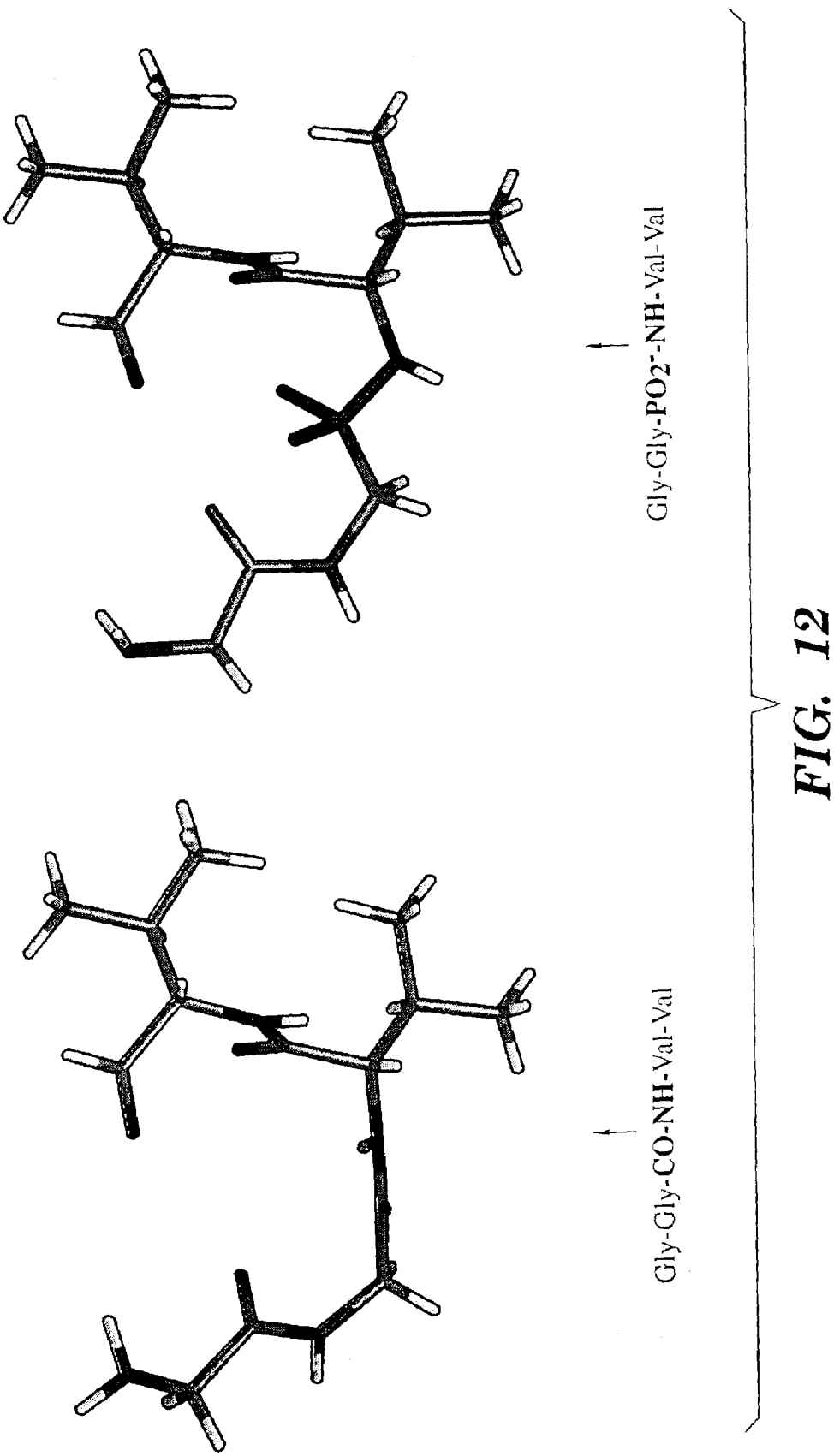
FIG. 12 is a structural comparison of the native β-amyloid peptide and the transition state phosphonamidate β-amyloid peptide which has the peptide link between Gly 38 and Val 39 replaced with a phosphonamidate bond.

An antibody combining site complementary to the tetrahedral transition state analog on the right of FIG. 12, will force the normally planar bond of the Aβ substrate peptide on the left into a transition state-like conformation. Such bond distortion is expected to catalyze the hydrolytic cleavage of the Aβ peptide at the Gly$_{38}$-Val$_{39}$ linkage.

Immunization with Transition State Peptide Antigens

Peptide antigens were coupled to the immunogenic carrier KLH prior to immunization of mice. Standard protocols were used to immunize BALB/c mice with the KLH-linked Aβ peptides described in the preceding sections. Briefly this procedure used i.p. injection of the different antigens emulsified in complete Freunds adjuvant, followed by a second course in incomplete Freunds adjuvant. Three days prior to hybridoma fusion, the BALB/c mice were boosted i.v. with antigen in PBS.

A hybridoma fusion was performed using the spleen of a mouse immunized with either a mixture of the phenylalanine statine transition state antigens generated (FIG. 7), a mixture of the statine (Sta) transition state Aβ antigens generated (FIG. 6), the reduced peptide bond transition state Aβ antigen generated (transition state mimic located between Phe$_{19}$-Phe$_{20}$), or the phosphoamidate transition state Aβ antigen generated (transition state mimic located between Gly$_{38}$-Val$_{39}$). Monoclonal antibodies listed in Table 8 were generated from these mice.

TABLE 8

| Analog Used | Bonds Modified | Potential Cleavage Sites | Antibodies Generated |
| --- | --- | --- | --- |
| statine | Val$_{39}$-Val$_{40}$ | Val$_{39}$-Val$_{40}$ | 2B2, 2H6, 3F2, 4D3, 6A6, |
|  | Val$_{40}$-Ile$_{41}$ | Val$_{40}$-Ile$_{41}$ | 1E4, 11E9, 9D6, 5C7, 7C7, |
|  | Ile$_{41}$-Ala$_{42}$ | Ile$_{41}$-Ala$_{42}$ | 1D12 |

TABLE 8-continued

| Analog Used | Bonds Modified | Potential Cleavage Sites | Antibodies Generated |
|---|---|---|---|
| phenylalanine-statine | $Phe_{19}$-$Phe_{20}$<br>$Phe_{20}$-$Ala_{21}$ | $Phe_{19}$-$Phe_{20}$<br>$Phe_{20}$-$Ala_{21}$ | 6E2, 5A11, 6F11, 2E3, 8E3, 5G4, 4C7, 8D12, 2C12, 4G7, 5C7, 3C1, 4H9, 8E6, 1H2, 3B1, 2H11 |
| reduced peptide bond | $Phe_{19}$-$Phe_{20}$ | $Phe_{19}$-$Phe_{20}$ | 6E7, 6F6 |
| phospho-amidate | $Glu_{38}$-$Val_{39}$ | $Gly_{38}$-$Val_{39}$ | in progress |

Demonstration of Aβ Binding by Generated Antibodies

It was very important to demonstrate that the anti-Aβ and anti-transition state Aβ monoclonal antibodies bound to the natural $A\beta_{1-43}$ peptide which they were designed to sequester or cleave. To do this, $A\beta_{1-40}$ and $A\beta_{1-43}$ were radiolabeled with $^{125}I$ and the iodinated peptide was then separated from unlabeled material by HPLC. Probe was incubated with either purified anti-Aβ antibodies or media taken from hybridoma clones producing anti-Aβ antibodies. The amount of $^{125}I$-$A\beta_{1-43}$ bound to antibody was determined using a polyethylene glycol separation method. Results of the experiment are presented in Table 3.

The data in Table 3 demonstrate the ability of the purified 5A11 monoclonal anti-Aβ antibody to bind a high percent of $^{125}I$-$A\beta_{140}$ This binding assay was used to screen clones and purified antibodies (Table 3) for their ability to bind Aβ. Similar procedures can also serve as the basis for a competitive displacement assay to measure the relative binding strength of different unlabeled Aβ peptides. (Note: with very efficient catalytic antibodies this binding assay may have to be performed on ice to ensure that no cleavage of Aβ occurs during the 1 h incubation time.) The assay rapidly identified clones producing high affinity anti-Aβ antibodies.

Monoclonal antibodies from hybridomas obtained using the phenylalanine statine transition state Aβ-KLH antigen were screened by ELISA to assess their binding to both the normal $A\beta_{1-43}$ peptide and to the phenylalanine statine transition state Aβ peptide. Two major patterns were found (FIG. 13).

One group of antibodies (the left portion of FIG. 13) bound to the immunizing transition state peptide and cross-reacted strongly with the native $A\beta_{1-43}$ peptide (each was adsorbed directly onto the ELISA plate). The second group (the right portion) showed a high binding preference for the phenylalanine statine transition state Aβ peptide and reacted minimally with native $A\beta_{1-43}$.

Figure 13:
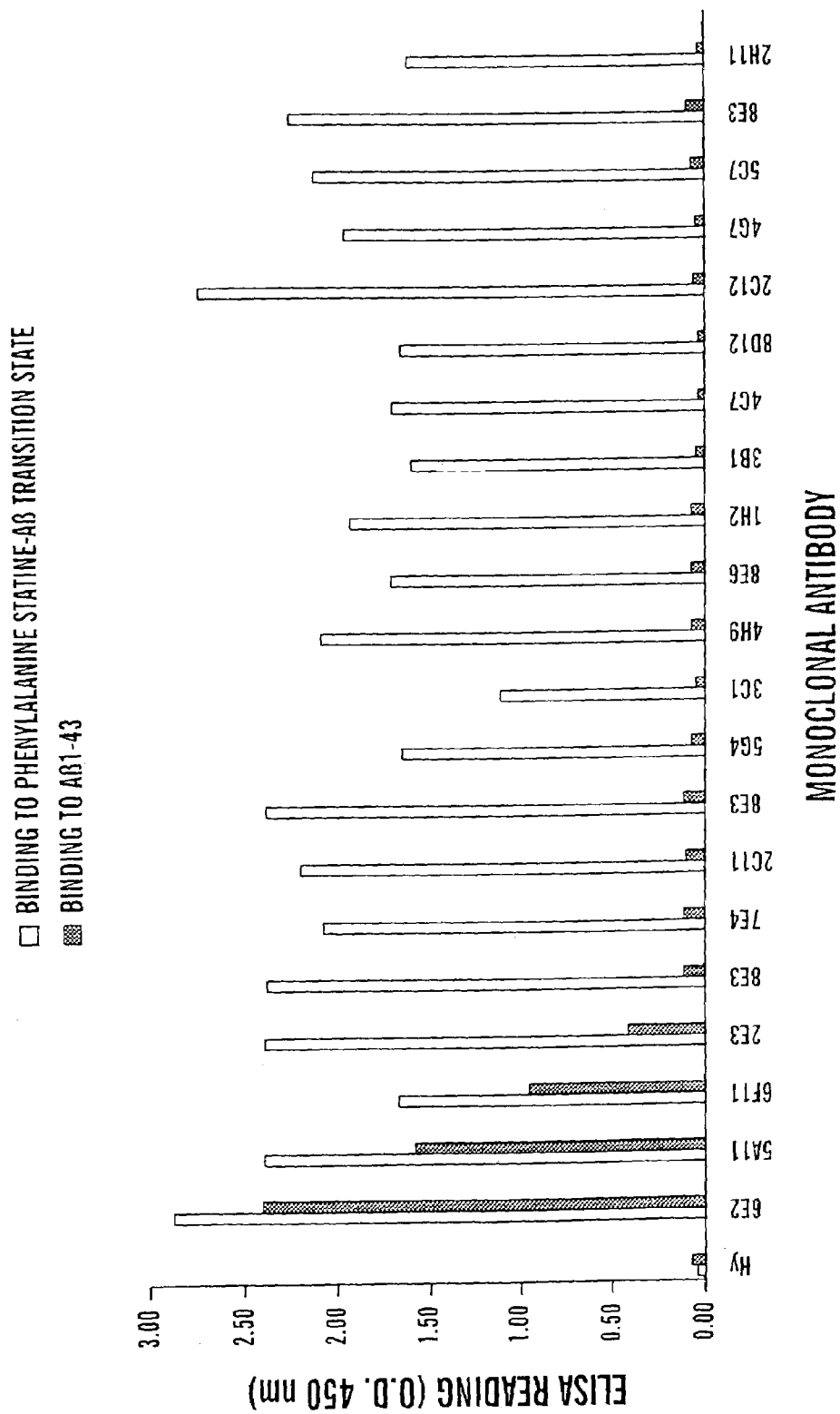
FIG. 13 is a diagrammatic representation of data from an ELISA which assess the binding of monoclonal antibodies generated to transition state β-amyloid peptide analogs, to the normal Aβ$_{1-43}$ and to the phenylalanine statine transition state β-amyloid peptide.

Strong color reactions were obtained in this ELISA using only 10 μl of hybridoma supernatant while Hy media alone or PBS gave a low background (FIG. 13). These results demonstrate that the comparative ELISA screen, although only a semi-quantitative measure of binding, provides a means for identifying monoclonal antibodies that are highly selective for, and most reactive with, the transition state. Importantly, the experiment was performed with carrier-free Aβ peptides adsorbed directly onto microtitre plates, indicating antibody specificity for Aβ peptide rather than carrier.

These findings indicate that several of the generated anti-Aβ transition state antibodies were unique. They bound to both the phenylalanine statine- and normal-Aβ peptides. Their selective recognition of the transition state and weaker cross-reaction with native $A\beta_{1-43}$ however indicates that this binding interaction is very different from that shown by conventional anti-native Aβ antibodies. It further indicates that these new antibodies may be able to force the native Aβ peptide into a conformation resembling the transition state for hydrolytic cleavage. Importantly, some of the antibodies which showed only minimal binding to $A\beta_{1-43}$ in this ELISA, did display cross-reactivity with the natural peptide using a highly sensitive $^{125}I$-$A\beta_{1-43}$ binding assay (Table 3).

Figure 14:
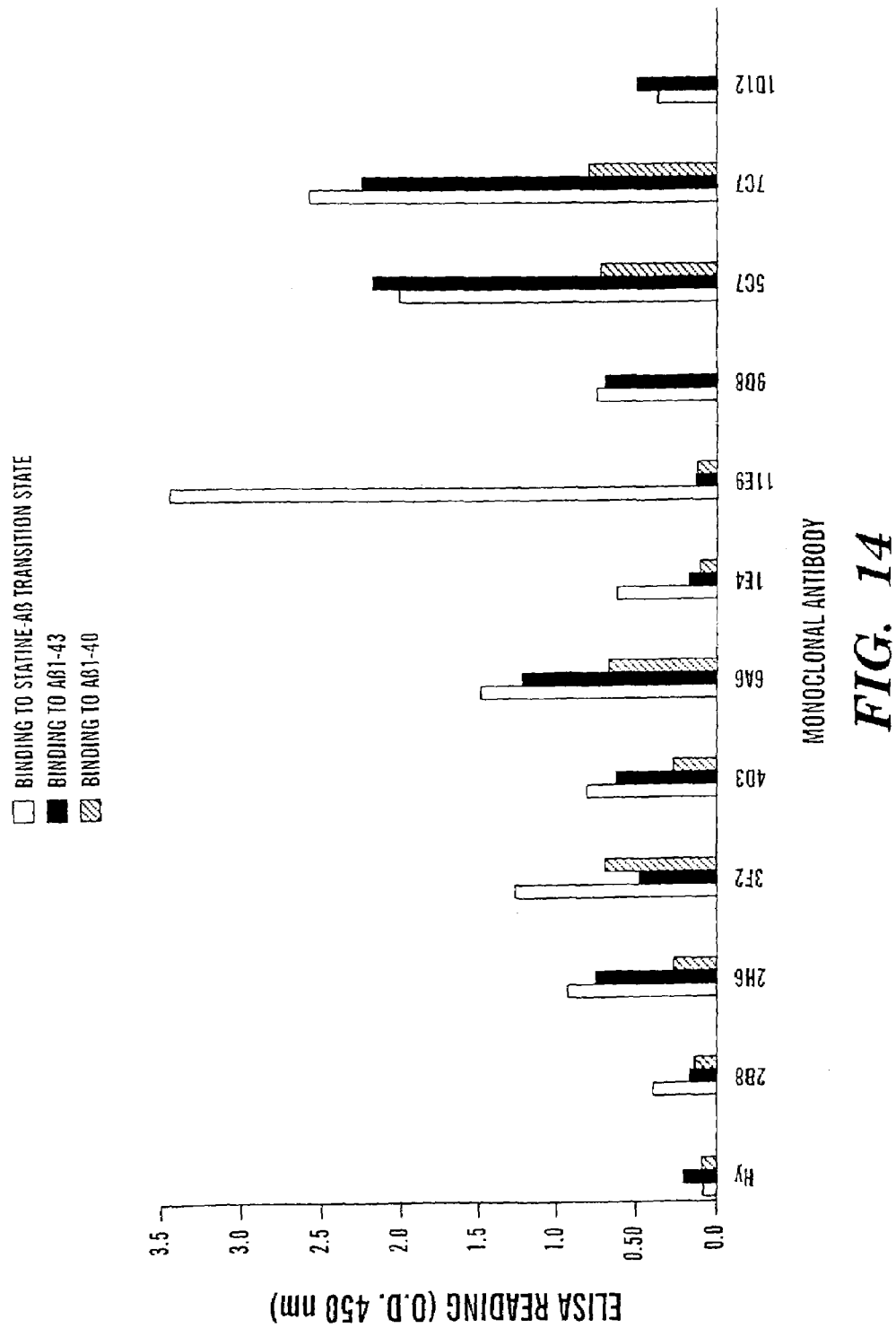
FIG. 14 is a diagrammatic representation of data from an ELISA comparing antibody binding to the statine transition state β-amyloid peptide versus native Aβ$_{1-43}$ and native Aβ$_{1-40}$.

ELISAs were also performed to investigate the binding of anti-statine analog antibodies to both the normal $A\beta_{1-43}$ peptide and to the statine transition state Aβ peptide (FIG. 14). The antibodies bound to the C-terminal locus on these carrier-free Aβ peptides (adsorbed directly to the microtitre plate) confirming their anti-peptide specificity. Most of the antibodies preferentially recognized the statine Aβ transition state, but cross-reacted with native $A\beta_{1-43}$. This indicates that these new antibodies are able to force the native Aβ peptide into a conformation resembling the transition state for hydrolytic cleavage of its C-terminal amino acids. Such cleavage is predicted to convert $A\beta_{1-43}$ into potentially less harmful shorter peptides, like $A\beta_{1-40}$ or $A\beta_{1-39}$.

Clone 11E9 had the strongest preference for the statine analog and may be the most likely to have catalytic activity (FIG. 14). Several clones displayed no difference in their reactivity with the native versus statine transition state Aβ peptide. The clones were also tested with $A\beta_{1-40}$ to identify antibodies which do not react with this shortened, 40 amino acid version of Aβ (FIG. 14). Used therapeutically, such antibodies should preferentially bind/cleave the less abundant, but more noxious $A\beta_{1-43}$ species in the blood as opposed to the smaller and less detrimental $A\beta_{1-40}$.

Solid Phase and TLC Aβ Proteolytic Assays

Figure 15:
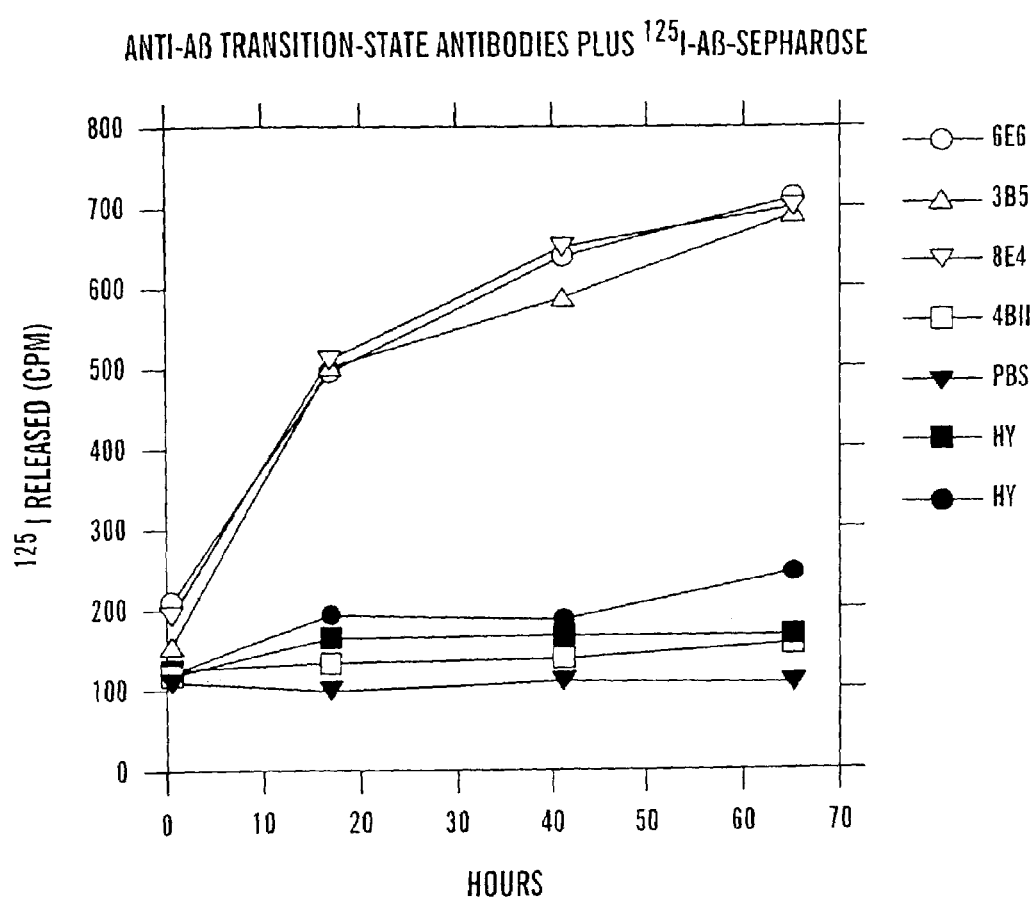
FIG. 15 is a graph of data showing the cleavage of $^{125}$I-Aβ-sepharose by monoclonal antibodies generated to transition state analogs of β-amyloid.

A solid phase $^{125}I$-labeled Aβ assay was developed to screen anti-transition state antibody hybridoma supernatants for specific proteolytic activity. The peptide Cys-His-Gln-Lys-Leu-Val-Phe-Phe-Ala-Glu-Asp-Val-Gly-Tyr-amide (SEQ ID NO: 5) which encompasses amino acids 14-25 of Aβ was radiolabeled and coupled to a thiol-reactive, iodoacetyl-Sepharose gel to form an irreversible linkage. The product was incubated with phenylalanine-statine anti-transition state antibody and assayed for the progressive release of soluble $^{125}I$-peptide from the solid phase matrix. Release of radioactivity from the $^{125}I$-Aβ-Sepharose was used to identify catalytic activity (FIG. 15). The assay was verified by the ability of several different proteases to rapidly hydrolyze this Sepharose-linked Aβ substrate. The peptide was readily accessible to proteolytic cleavage as revealed by a release of soluble 125I-peptide that increased with incubation time.

The results presented in FIG. 15 indicate that the antibody-containing media of several clones released $^{125}I$-peptide at a greater rate than other clones from this fusion or the PBS and Hy medium controls. Large amounts of these antibodies can be obtained, purified and tested at higher concentrations to achieve much faster rates of cleavage and to verify that the antibodies are acting in a catalytic mode using conventional enzyme kinetics. By changing the composition of the $^{125}$I-peptide this same strategy can be used to assay antibodies reactive with different regions of Aβ.

A thin layer chromatography-based autoradiography assay was devised to obtain more definitive evidence for antibody-mediated cleavage of Aβ. Selected anti-phenylalanine statine Aβ transition state clones were expanded and ascites production induced. The different monoclonal antibodies were isolated using protein A-Sepharose. Two $^{125}$I-labeled peptides, Aβ$_{1-40}$ and a 17-mer, encompassing amino acids 9-25 of Aβ, were used to test for peptide cleavage. The antibodies were added to the $^{125}$I-peptides, allowed to incubate and the reaction mix spotted onto polyamide thin layer sheets which were then developed in different solvents. The migration of $^{125}$I-products was followed by exposing the sheet using a quantitative phosphoimager system Quantitation of the different labeled peptide fragments produced indicated that addition of the antibodies to the Aβ peptides lead to significant break down of the Aβ peptides compared to the untreated peptides (PBS).

Disaggregation of β-amyloid by Monoclonal Antibodies

The self-aggregation of synthetic Aβ peptides has been shown previously to lead to microscopic structures resembling amyloid plaques in the brain (Solomon et al., *Proc. Natl. Acad. Sci. USA* 94: 4109-12 (1997); Solomon et al., *Proc. Natl. Acad. Sci. USA* 93: 452-5 (1996)) which exhibit the same bright green fluorescence upon exposure to thioflavin T. These aggregates are very stable and usually require harsh detergents or strong acids to dissolve. However, it has been demonstrated that the binding of certain anti-Aβ monoclonal antibodies can effectively inhibit the initial aggregation of this peptide and also disaggregate preformed Aβ complexes (Solomon et al., *Proc. Natl. Acad. Sci. USA* 94: 4109-12 (1997); Solomon et al., *Proc. Natl. Acad. Sci. USA* 93: 452-5 (1996)).

A radioactive assay was used to quickly screen the different monoclonal antibodies produced by the present experiments for an ability to dissolve preformed Aβ aggregates, made with $^{125}$I-labeled and unlabeled soluble Aβ peptide. An aliquot of the labeled aggregate was incubated with either PBS, the 5A11 anti-Aβ antibody or an equal amount of an irrelevant mouse antibody (7D3, anti-human transferrin receptor), and the level of released radioactivity was subsequently measured (Table 9). The Aβ-specific 5A11 antibody solubilized 80% of the Aβ aggregates while an equal amount of the control antibody had only a minor effect, suggesting that the equilibrium was displaced by antibody-mediated binding of soluble Aβ.

TABLE 9

Solubilization of $^{125}$I-β$_{1-40}$ Aggregate by Monoclonal Anti-Aβ Antibody

| Addition | $^{125}$I-Aβ$_{1-40}$ in Ppt. (cpm) | Amount Solubilized (% of PBS Control) |
|---|---|---|
| PBS control | 3,420 | — |
| +5A11 anti-Aβ | 676 | 80 |
| +7D3 anti-TfR | 2,458 | 27 |

Production of Vectorized Anti-Aβ/Anti-Receptor Bispecific Antibodies

Anti-Aβ antibodies were linked to anti-transferrin receptor antibodies (anti-TfR) which served as vectors for delivery of the anti-AS antibodies into the brain. The 7D3 mouse monoclonal antibody was used as the anti-TfR part of the construct. 7D3 is specific for the human receptor and selectively immunostains cortical capillaries in normal human brain tissue (Recht et al., *J. Neurosurg.* 72: 941-945 (1990)). Antibody attachment to the receptor is not blocked by an excess of human transferrin. The epitope recognized by this antibody is therefore distant from the receptor-ligand binding site. Bispecific antibodies constructed with this 7D3 antibody and an anti-Aβ antibody are predicted to be useful for therapy in patients with Alzheimer's disease.

For studies in mouse models of Alzheimer's disease an anti-mouse transferrin receptor monoclonal antibody produced in the rat was obtained. This antibody also appears to recognize a transferrin receptor epitope which does not involve ligand binding. The antibody therefore has no effect on cell proliferation when using murine lines.

Figure 16:
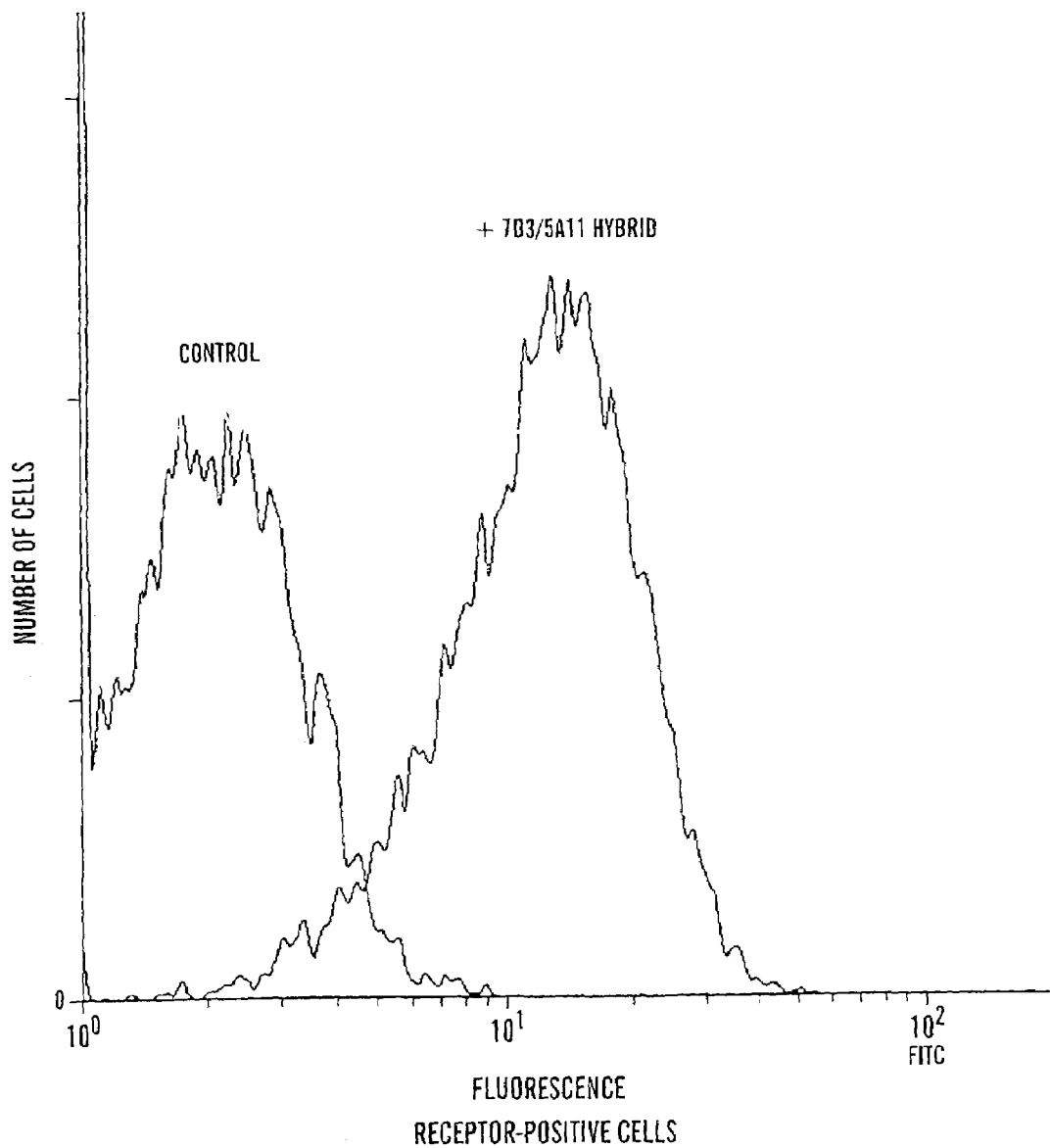
FIG. 16 is a diagrammatic representation of data which quantitate the attachment of bispecific antibody to receptor-positive cells.

A series of functional assays were performed after completion of the synthesis, purification and size analysis of the anti-Aβ/anti-transferrin receptor bispecific antibodies. The vectorized bispecific antibody, composed of a rat monoclonal antibody directed against the mouse transferrin receptor plus the 5A11 mouse anti-Aβ monoclonal antibody, was tested for the ability to attach to transferrin receptor bearing mouse cells. Both components of the bispecific antibody were detected on the cell membrane by cytofluorimetry (FIG. 16) when this duplex was reacted with transferrin receptor positive mouse cells and probed using either a rat IgG-specific or mouse IgG-specific fluorescent secondary antibody reagent.

The capacity of the hybrid reagent to bind $^{125}$I-Aβ compared favorably with that of the parent anti-Aβ antibody (Table 10).

TABLE 10

$^{125}$I-Aβ Binding to Bispecific Antibody

| Addition | $^{125}$I-Aβ$_{1-40}$ Bound (cpm) |
|---|---|
| Control | 4,199 |
| +anti-Aβ | 23,301 |
| +anti-Aβ/anti-receptor | 22,850 |

To ensure that both of these binding activities resided on the bispecific antibody, transferrin receptor positive cells were treated with the hybrid reagent, unbound material was washed away, and then the cells with bound antibody was exposed to $^{125}$I-Aβ$_{1-40}$. After washing away unbound Aβ, the cell-bound radioactivity was compared to control cells which had been identically prepared except for omission of pretreatment with bispecific antibody. The results are presented in Table 11, and verify the dual specificity of this bispecific antibody by clearly showing that it can simultaneously attach to the cell membrane and bind $^{125}$I-Aβ$_{1-40}$.

TABLE 11

Bispecific Antibody-Mediated Binding of $^{125}$I-Aβ to Receptor-Positive Cells

| Pretreatment of Cells | $^{125}$I-Aβ$_{1-40}$ Bound (cpm) |
|---|---|
| None | 2,367 |
| +anti-Aβ/anti-transferrin receptor | 11,476 |

Transcytosis of Bispecific Antibody into the Brain

A rat monoclonal anti-mouse transferrin receptor antibody was coupled to a mouse monoclonal antibody (obtained from American Type Culture Collection (ATCC TIB 219), also designated R17 217.1.3 (*Cell. Immunol.* 83: 14-25 (1984)), so that the entry of this new vectorized bispecific construct into brain could be monitored. The bispecific antibody was labeled with $^{125}$I and injected i.v. into normal mice. After different lengths of time the mice were sacrificed and the amount of $^{125}$I-bispecific antibody that crossed the blood-brain barrier and entered the brain was gauged by a mouse capillary depletion method (Friden et al., *J. Pharm. Exper. Ther.* 278: 1491-1498 (1996); Triguero et al., *J. Neurochem.* 54: 1882-1888 (1990)).

Figure 17:
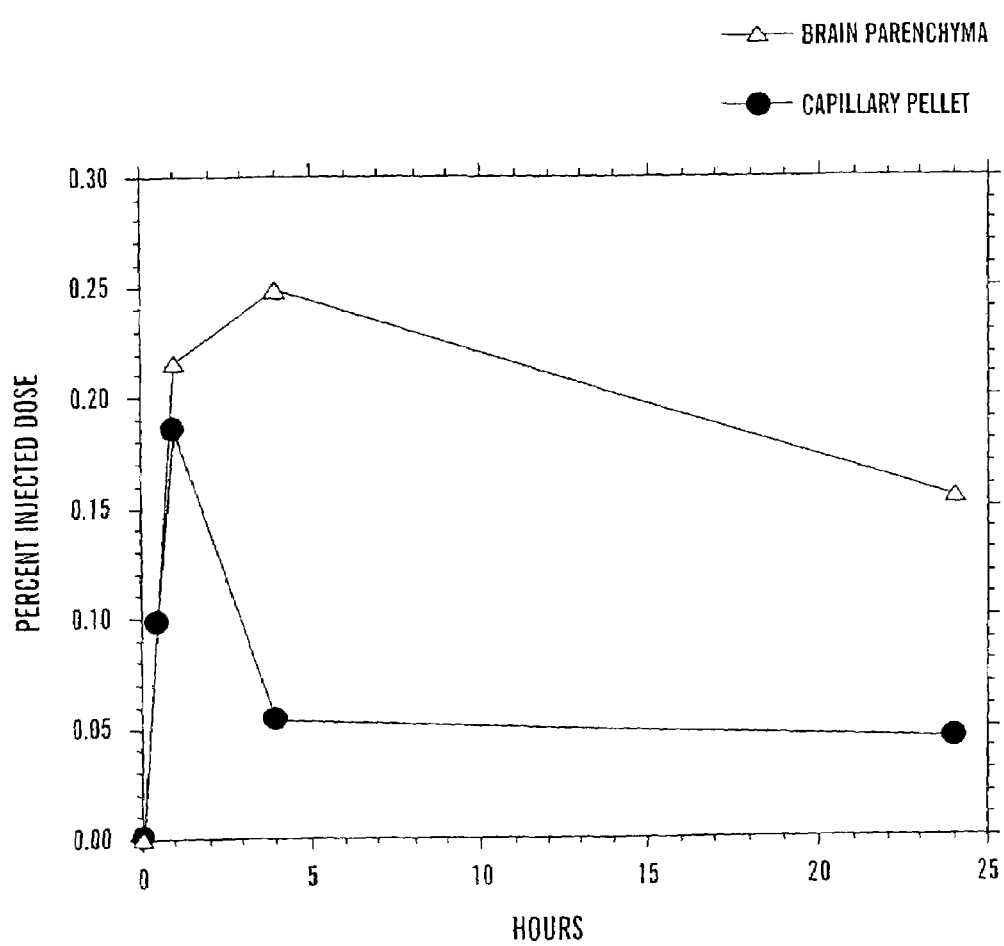
FIG. 17 is a diagrammatic representation of data obtained from experiments designed to track the transcytosis of vectorized bispecific antibody into brain.

The amount of vectorized bispecific antibody found in the brain parenchyma or brain capillary fractions was measured following differential density centrifugation of the brain homogenate. These values were plotted as a function of time after i.v. injection (FIG. 17). The time-dependent redistribution of radiolabeled bispecific antibody from the capillaries and into the parenchyma was consistent with its passage across the cerebral endothelial blood-brain barrier (Joachim et al., *Nature* 341: 6239:226-30 (1989)). Even greater accumulation in the parenchyma is expected to occur if the antibodies attach to Aβ in the cerebral plaques of plaque-bearing mice.

Monitoring the Brain Distribution of Bispecific Antibody in Live Mice

The ability to follow the entry and accumulation of vectorized bispecific antibodies in the brain of live mice would greatly assist in the development of the intracerebral treatment of plaque-bearing mice. Such a development would enable time-course studies and would greatly reduce problems with inter-mouse variability. Preliminary studies with $^{125}$I-labeled bispecific antibodies were performed to determine if immunoscintigraphy was feasible in this system. As a first step, either the radiolabeled vectorized bispecific antibody ($^{125}$I-R17/5A11) or a non-vectorized control bispecific antibody were administered to separate mice. Sequential brain images were accumulated at 1, 6, 24 and 48 hours following i.v. administration of the $^{125}$I-labeled bispecific antibody probes. Although this technique suffered from a difficulty in determining how much of the signal was due to the levels of blood-borne radioactivity circulating through the brain, significant distinctions were noted in the brain of mice treated with the mouse transferrin receptor reactive bispecific antibody versus those receiving the control bispecific antibody. When the vectorized agent was used, brain levels increased between 1 and 6 hrs and then declined to a much lower level at 24 and 48 hrs. Mice treated with the control displayed no increase between 1 and 6 hrs. The reason for decreased brain levels at 24 hrs and beyond is not known but might be due to dehalogenation of the bispecific antibody probes so that free $^{125}$I is released. Alternative methods utilizing radioactive labels such as $^{111}$In (Sheldon et al., *Nucl. Med. Biol.* 18: 519-526 (1991)) or $^{99m}$Tc (Texic et al., *Nucl. Med. Biol.* 22: 451-457 (1995)) attached to the vectorized bispecific antibody can be utilized in future experiments if the use of iodine presents a technical problem. This imaging technology will be useful for determining if smaller vectorized bispecific antibodies (eg. F(ab')$_2$) with different physical properties and an altered biodistribution will penetrate into the brain more effectively.

F(ab')$_2$ Heterodimers for Vector-Mediated Transport into the Brain

The introduction of whole antibodies into the brain might be detrimental if they were to fix complement and promote complement-mediated lysis of neuronal cells. The development of smaller vectorized F(ab')$_2$ bispecific reagents is expected to avoid this problem. It has been shown that aggregated Aβ itself can fix complement in the absence of any antibody and that the resulting inflammation may contribute to the pathology of Alzheimer's disease. The possibility of intracerebral antibody having a similar effect would be greatly reduced by eliminating the Fc region of the antibody. Moreover, since coupling of Fab' halves uses the intrinsic hinge region cysteines, no extraneous substituent linkage groups need be added.

Faster or more efficient entry into the brain represents another potential advantage that smaller F(ab')$_2$ or Fv$_2$ reagents provide for intracerebral delivery. Such modified bispecific agents can be prepared and compared to full-sized hybrid antibodies for their relative effectiveness in reaching the brain, crossing the blood-brain barrier, and affecting Aβ plaque development, by the methods described herein. It is important to note, however, that only minor differences were found when the capacity of differently-sized anti-transferrin receptor bispecific reagents for delivering toxins into cells by receptor-mediated endocytosis was compared (Raso et al., *J. Biol. Chem.* 272: 27623-27628 (1997)). This observation might indicate that little variation will be seen for transcytosis across the brain capillary endothelial cells which form the blood-brain barrier. At the very least however one would expect the two types of vectorized molecules to have different biodistribution and plasma half-life characteristics (Spiegelberg et al., *J. Exp. Med.* 121: 323 (1965)).

Methods of the Invention

Antigen Synthesis. The statine and phenylalanine statine transition state peptides were synthesized using automated Fmoc chemistry. Peptide synthesis was designed so that a mixture of all possible modifications would automatically result. Fmoc-statine (Sta), [N-Fmoc-(3S, 4S)-4-amino-3-hydroxy-6-methyl heptanoic acid] and Fmoc-"phenylalanine statine" (PhSta), [N-Fmoc-(3S ,4S )-4-amino-3-hydroxy-5-phenylpentanoic acid] were purchased commercially. Each peptide was tested for purity by HPLC and its composition was verified by mass spectral and amino acid analysis.

The design strategy and methods for synthesizing phosphonamidate- and phosphonate-based transition state peptides are straightforward (Bartlett et al., *Am. Chem. Society* 22: 4618-4624 (1983); Bartlett et al., *Biochemistry* 26: 8553-8561 (1987)). The N-terminal portion of the peptide (N-acetyl-Cys-Met-Val-Gly) was made using standard automated Fmoc chemistry. After cleavage from the resin the N-acetyl tetrapeptide was treated with pyridine disulfide to protect its sulfhydryl group. An acid chloride of Cbz-glycine phosphonate monomethyl ester (Bartlett et al., *Am. Chem. Society* 22: 4618-4624 (1983); Bartlett et al., *Biochemistry* 26: 8553-8561 (1987)) was coupled with Val-Val-Ile-Ala-amide which was synthesized by automated Fmoc chemistry. The last amino acid of Aβ, Thr, was omitted due to potential problems with its unprotected hydroxyl group. The product, Cbz-Gly-PO$_2^-$-NH-Val-Val-Ile-Ala-amide has a phosphonamidate (methyl ester) bond between the Gly and Val residues. Next, the Cbz blocking group was removed using hydrogen so that the protected N-acetyl-Cys-Met-Val-Gly peptide could be added to the amino terminal end of this transition state peptide by HBTU-activated peptide linkage. Treatment with mercaptoethanol and rabbit liver esterase was used to deblock the peptide. Each key component in the synthetic scheme was tested for purity by HPLC and its composition was verified by mass spectral and amino acid analysis.

A reduced peptide bond linkage was placed at the indicated sites in the Aβ molecule. Automated Fmoc chemistry was used to begin synthesis of the peptide. A pre-synthesized Fmoc amino aldehyde was then added manually and after the imide was reduced, automated synthesis was resumed (Meyer et al., *J. Med. Chem.* 38: 3462-3468 (1995)).

Coupling of Antigen to Carrier. The native and transition state Aβ peptides were coupled to maleimide-activated KLH by standard procedures (Partis et al., *J. Pro. Chem.* 2: 263-277 (1983)), in order to elicit an immune response. A Cys residue was strategically placed at the N- or C-terminal end of the peptides to provide a suitable linkage group for coupling them via a thioether bond to maleimide activated carrier proteins. This stable linkage attaches the peptide in a defined orientation. Addition of ~20 peptides/KLH has been obtained based upon the transition state amino acid content as determined by amino acid analysis of the hydrolyzed conjugates (Tsao et al., *Anal. Biochem.* 197: 137-142 (1991)).

Immunization of Mice. Standard protocols were used to immunize mice with the KLH-linked Aβ peptides described in the preceding sections. Briefly this procedure used i.p. injection of the different antigens emulsified in complete Freunds adjuvant, followed by a second course in incomplete Freunds adjuvant. Three days prior to the hybridoma fusion, the BALB/c mice were boosted i.v. with antigen in PBS. After ~1 month animals were given a boost i.p. using the antigen emulsified with incomplete adjuvant. Serum from these animals was analyzed for anti-peptide antibodies by ELISA. BALB/c mice showing abundant antibody production were boosted by an i.v. injection with antigen and three days later they were used to generate hybridoma clones that secrete monoclonal antibodies.

None of the mice immunized with Aβ vaccines or the anti-Aβ ascites-producing mice displayed ill effects even though some of those induced antibodies cross-react with mouse Aβ and mouse amyloid precursor protein.

Hybridoma Production I. A hybridoma fusion was performed using the spleen of a mouse immunized with the phenylalanine statine transition state Aβ-KLH antigen. Spleen cells from mice with the highest titre were fused with mouse myeloma NS-1 cells to establish hybridomas according to standard procedures (Köhler et al., *Nature* 256: 495 (1975); R. H. Kennett, Fusion Protocols. Monoclonal Antibodies, eds. R. H. Kennett, T. J. McKearn and K. B. Bechtol. Plenum Press, New York. 365-367 pp. (1980)).

$^{125}$I-Aβ Binding Assay. Aβ$_{1-40}$ and Aβ$_{1-43}$ were radiolabeled with $^{125}$I and the iodinated peptide then separated from unlabeled material by HPLC to give quantitative specific activity (~2000 Ci/mmol) (Maggio et al., *Proc. Natl. Acad. Sci.* 89: 5462-5466 (1992)). This probe was incubated for 1 h at 23° C. with either purified anti-Aβ antibodies or media taken from hybridoma clones producing anti-Aβ antibodies. A polyethylene glycol separation method was used to detect the amount of $^{125}$I-Aβ$_{1-43}$ bound to antibody. By using serial dilution, this assay can provide relative binding affinities for the different hybridoma supernatants or purified antibodies.

Solid Phase Aβ Proteolytic Assay. A solid phase $^{125}$I-labeled Aβ assay was developed to screen anti-transition state antibody hybridoma supernatants for specific proteolytic activity. The Cys-His-Gln-Lys-Leu-Val-Phe-Phe-Ala-Glu-Asp-Val-Gly-Tyr-amide peptide (SEQ ID NO: 5) encompassing amino acids 14-25 of Aβ was radiolabeled with $^{125}$I and the iodinated peptide was then separated from unlabeled material by HPLC. The highly radioactive Aβ peptide was coupled to a thiol-reactive, iodoacetyl-Sepharose gel to form an irreversible linkage. Antibodies were added to the labeled Aβ, which was then assayed for progressive release of soluble $^{125}$I-peptide from the solid phase matrix at pH 7, 25° C. This assay was verified by the ability of several different proteases in to rapidly hydrolyze this Sepharose-linked Aβ substrate. Release of soluble $^{125}$I-peptide increased with incubation time.

Although Aβ is cleaved by several naturally occurring proteases, preliminary tests indicated that interference from high levels of background hydrolysis was not a problem when assaying hybridoma supernatants of clones that did produce catalytic antibodies. A further precaution that can be taken against exogenous proteases is carrying out all hybridoma cell fusions and cell culturing in serum-free media.

TLC Aβ Proteolytic Assay. A thin layer chromatography-based autoradiography assay was used to obtain more definitive evidence for antibody-mediated cleavage of Aβ. Selected anti-phenylalanine statine Aβ transition state clones were expanded and ascites production induced. The different monoclonal antibodies were isolated using protein A-Sepharose. The cleavage assay used $^{125}$I-Aβ$_{1-40}$ and an $^{125}$I-labeled 17-mer, encompassing amino acids 9-25 of Aβ. Binding of the two $^{125}$I-labeled peptides to the purified monoclonal antibodies 5A11 and 6E2 was examined using either a PEG precipitation assay or by a co-electrophoresis method. Peptide cleavage was tested by adding the antibodies to the $^{125}$I-peptides, incubating and then spotting the reaction mix onto polyamide thin layer sheets. The chromatographs were developed in different solvents (eg. 0.5 N HCl, 0.5 N NaOH or pH 7 phosphate buffer) and the migration of $^{125}$I-products was followed by exposing the sheet using a quantitative phosphoimager system.

Screen and Isolate Select Anti-Aβ Antibodies. An ELISA was used to initially screen for anti-Aβ and anti-transition state Aβ peptide monoclonal antibodies. Both the transition state peptide and the corresponding natural Aβ peptide were adsorbed onto separate microtitre plates. The hybridoma supernatants were screened using two assays so that the relative binding to both native and transition state Aβ peptides could be quantitated. Clones producing monoclonal antibodies that preferentially recognized the transition state or bound Aβ with high affinity were selected for expansion and further study.

Propagation and Purification of Monoclonal Antibodies. Selected clones producing anti-Aβ antibodies and clones producing anti-receptor antibodies were injected into separate pristane-primed mice. Ascites were collected and the specific monoclonal antibodies isolated. Purification of antibodies from ascites was accomplished using a Protein A column or alternatively, antibodies were isolated from ascites fluid by $(NH_4)_2SO_4$ precipitation and passage over an S-300 column to obtain the 150 kDa immunoglobulin fraction. Monovalent Fab fragments were prepared and isolated by established methods. Their purity was evaluated by SDS-PAGE under reducing and non-reducing conditions. 50-100 mg of purified monoclonal antibody was routinely obtained from each ascites-bearing mouse.

Further Characterization of Catalytic Activity on Aβ Substrates. To fully define the hydrolytic properties of the isolated anti-transition state antibodies some very important controls can be run. First the ability to completely block catalytic antibody activity with the appropriate transition state peptide can be verified. This non-cleavable "inhibitor" should bind much more tightly to the antibody combining sites and thereby prevent substrate binding or cleavage. Substrate specificity can be further established by showing no cleavage of a sham Aβ peptide having a different amino acid sequence.

The products of hydrolysis can also be fully characterized by HPLC, amino acid and mass spectral analysis. Control antibodies that are not directed against the transition state Aβ can be tested and confirmed to produce no catalysis. Finally, catalytic activity can be shown to reside in the purified Fab fragments of the anti-transition state antibody.

Purified Anti-Aβ Antibodies Dissolve Preformed Aβ Aggregates. (Walker et al., Soc. Neurosci. Abstr. 21: 257 (1995), Zlokovic, B. V., Life Sciences 59: 1483-1497 (1996)). Aβ precipitates were formed and measured in vitro (Yankner et al., Science 250: 279-282 (1990), Kowall et al., Proc. Natl. Acad. Sci. 88: 7247-7251 (1991)). A radioactive assay was used to quickly screen the different monoclonal antibodies produced for an ability to dissolve preformed Aβ aggregates. After adding $^{125}$I-Aβ to unlabeled soluble peptide, aggregates were formed by bringing the solution to pH 5 or by stirring it overnight in PBS. An aliquot of the labeled aggregate was incubated for 1 hr with either PBS, the 5A11 anti-Aβ antibody or an equal amount of an irrelevant mouse antibody (7D3, anti-human transferrin receptor). After centrifugation, the level of radioactivity in the precipitate was measured.

Generation of Vectorized Anti-Aβ/Anti-Receptor Bispecific Antibodies. The anti-Aβ antibodies were chemically coupled to anti-human transferrin receptor and anti-mouse transferrin receptor antibodies by different methods (Raso et al., J. Biol. Chem. 272: 27623-27628 (1997); Raso et al., Monoclonal antibodies as cell targeted carriers of covalently and non-covalently attached toxins. In Receptor mediated targeting of drugs, vol. 82. G. Gregoriadis, G. Post, J. Senior and A. Trouet, editors. NATO Advanced Studies Inst., New York. 119-138 (1984)). A rapid thioether linkage technique was used to form strictly bispecific hybrids using Traut's reagent and the heterobifunctional SMBP reagent. One component was sparingly substituted with thiol groups (SH). These readily reacted to form a thioether linkage upon mixture with the maleimido-substituted (M) second component following the reaction:

$$Ab_A\text{-SH} + Ab_B\text{-M} \rightarrow Ab_A\text{-S-}Ab_B$$

Gel filtration of the reaction mixture on an S-300 column yielded the purified dimer which was 300 kDa and had two sites for binding Aβ plus two sites for attachment to transferrin receptors on brain capillary endothelial cells. Non-targeted control hybrids were formed by linking a nonspecific MOPC antibody to the anti-Aβ antibody. This hybrid antibody does bind Aβ, but, being non-reactive with transferrin receptors, should not cross the blood-brain barrier.

F(ab')$_2$ fragments of the two different antibody types can similarly be thioether-linked to form Fc-devoid reagents that cannot bind complement which might otherwise cause neurotoxic effects. These smaller bispecific hybrids (100 kDa) can be formed by reducing the intrinsic disulfides which link the heavy chains of F(ab')$_2$ fragments (Raso et al., J. Immunol. 125: 2610-2616 (1980)). The thiols generated are stabilized and Ellman's reagent (E) is used to activate these groups on one of the components (Brennan et al., Science 229: 81-83 (1985)). Exclusively bispecific F(ab')$_2$ hybrids can be formed upon mixing the reduced Fab' with an activated Fab' having the alternate specificity according to the reaction:

$$\text{Fab}'_A\text{-SH} + \text{Fab}'_B\text{-SS-E} \rightarrow \text{Fab}'_A\text{-SS-Fab}'_B + \text{E-SH}$$

Purification on an S-200 column will isolate hybrids with one site for binding Aβ and one site for interaction with the target epitope on the brain capillary endothelial cells.

A similar approach can be used to make even smaller disulfide-linked single chain Fv heterobispecific dimers, Fv$_A$-SS-Fv$_B$ (50 kDa), to cross the blood-brain barrier. Soluble Fvs can be constructed to possess a carboxyl-terminal cysteine to facilitate the disulfide exchange shown in the reaction below, and create 50 kDa heterodimers exclusively:

$$Fv_A\text{-SH} + Fv_B\text{-SS-E} \rightarrow Fv_A\text{-SS-}Fv_B + \text{E-SH}$$

In side by side comparisons between whole antibody and either Fab' or Fv based bispecific reagents, the latter have proven to be moderately more effective on a molar basis for cell uptake via the transferrin receptor-mediated pathway (Raso et al., J. Biol. Chem. 272: 27623-27628 (1997)). Since these smaller constructs are monovalent for the cell-surface epitope, those findings dispel the notion that cross-linking of two surface receptors is necessary for the cellular uptake of immunocomplexes.

Functional Assays for Dual Binding Activity of Bispecific Antibodies. The capacity of the hybrid reagent to bind $^{125}$I-Aβ was compared with that of the parent anti-Aβ antibody in a standard PEG binding assay (see Table 10 for binding assays).

The ability of the appropriate bispecific antibodies to attach to transferrin receptor bearing human or mouse cells was confirmed by cytofluorimetry. The bispecific antibody was reacted with transferrin receptor positive human or mouse cells and probed using either a rat IgG-specific or mouse IgG-specific fluorescent secondary antibody reagent.

Measurement of Aβ Binding Using $^{125}$I-Aβ and a Polyethylene Glycol Separation. To ensure bispecificity, hybrid reagents were tested for a capacity to mediate the attachment of $^{125}$I-Aβ to receptor-bearing cells. Transferrin receptor positive cells were treated with the hybrid reagent, washed away unbound material and then exposed these cells to $^{125}$I-Aβ$_{1-40}$. The cells were washed and the amount of cell-bound radioactivity was compared to control cells which had been identically prepared except that pretreatment with bispecific antibody was omitted.

Capillary Depletion. The bispecific antibody was labeled with $^{125}$I and injected i.v. into normal mice. After different lengths of time the mice were sacrificed and the amount of $^{125}$I-bispecific antibody that crossed the blood-brain barrier and entered the brain was gauged by a mouse capillary depletion method (Friden et al., J. Pharm. Exper. Ther. 278: 1491-1498 (1996); Triguero et al., J. Neurochem. 54: 1882-1888 (1990)). The amount of vectorized bispecific antibody found in the brain parenchyma or brain capillary fractions was measured following differential density centrifugation of the brain homogenate. These values were plotted as a function of time after i.v. injection. Progressive passage from capillaries into the parenchyma indicates active transcytosis across the blood-brain barrier.

Immunoscintigraphy. A non-invasive method for monitoring intracerebral delivery process which involves visualizing the entry of a radiolabeled bispecific antibody into the brain of live mice, can also be used. Radiolabeled vectorized bispecific antibody ($^{125}$I-R17/5A11) or a non-vectorized control bispecific antibody were administered to separate mice. Sequential brain images were accumulated at 1, 6, 24 and 48 hours following i.v. administration of the $^{125}$I-labeled bispecific antibody probes. The animals were chemically immobilized during exposure using ketamine/xylazine anesthesia. This imaging technology could be very useful for determining if circulating anti-Aβ antibodies will prevent i.v. administered $^{125}$I-Aβ from entering the brain. Digital scintigraphy data was quantified using standards and the integration functions provided in the analysis software.

The invention claimed is:

1. A vectorized antibody which is characterized by the ability to catalyze the hydrolysis of β-amyloid at Val39-Val40, Phe19-Phe20 or Phe20-Ala21 of SEQ ID NO: 1, the vectorized antibody being produced by a method comprising immunizing an animal with a transition state analog which mimics the transition state that β-amyloid adopts during hydrolysis, the transition state analog being selected from a group consisting of statine and phenylalanine-statine.

2. The vectorized antibody of claim 1 which is a bispecific antibody.

3. The vectorized antibody of claim 2 which has a first specificity for the transferrin receptor and a second specificity for a transition state adopted by β-amyloid during hydrolysis and which is characterized by the ability to cross the blood brain barrier.

4. A method for generating antibodies which of catalyze the hydrolysis of β-amyloid at Val39-Val40, Phe19-Phe20 or Phe20-Ala21 of SEQ ID NO: 1, the method comprising the steps:

a) providing an antigen, the antigen being comprised of an epitope which mimics the conformation of a predetermined hydrolysis transition state of β-amyloid and selected from a group consisting of statine and phenylalanine-statine, and b) immunizing an animal with the antigen under conditions appropriate for the generation of antibodies to the hydrolysis transition state.

5. A vectorized antibody which is characterized by the ability to catalyze the hydrolysis of β-amyloid at Val39-Val40, Phe19-Phe20 or Phe20-Ala21 of SEQ ID NO: 1, and the ability to bind specifically to a transition state analog which mimics the transition state that δ-amyloid adopts during hydrolysis, the transition state analog being selected from a group consisting of statine and phenylalanine-statine.

6. The vectorized antibody of claim 5 which is a bispecific antibody.

7. The vectorized antibody of claim 6 which has a first specificity for the transferrin receptor and a second specificity for a transition state adopted by β-amyloid during hydrolysis.

8. An antibody which catalyzes hydrolysis of β-amyloid at Val39-Val40, Phe19-Phe20 or Phe20-Ala21 of SEQ ID NO: 1, the antibody being produced by a method comprising immunizing an animal with a transition state analog which mimics the transition state that β-amyloid adopts during hydrolysis, the transition state analog being selected from a group consisting of statine and phenylalanine-statine.

* * * * *

SEQUENCE LISTING

<160> NUMBER OF SEQ ID NOS: 7

<210> SEQ ID NO 1
<211> LENGTH: 43
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 2
<211> LENGTH: 17
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Cys

<210> SEQ ID NO 3
<211> LENGTH: 17
<212> TYPE: PRT
<213> ORGANISM: Homo sapiens

<400> SEQUENCE: 3

Cys Tyr Glu Val His His Gln Lys Leu Val Phe Phe Ala Glu Asp Val
1               5                   10                  15

Gly

<210> SEQ ID NO 4
<211> LENGTH: 10
<212> TYPE: PRT
<213> ORGANISM: Homo sapiens

<400> SEQUENCE: 4

Cys Met Val Gly Gly Val Val Ile Ala Thr
1               5                   10

<210> SEQ ID NO 5
<211> LENGTH: 14
<212> TYPE: PRT
<213> ORGANISM: Homo sapiens

<400> SEQUENCE: 5

Cys His Gln Lys Leu Val Phe Phe Ala Glu Asp Val Gly Tyr
1               5                   10

<210> SEQ ID NO 6
<211> LENGTH: 8
<212> TYPE: PRT
<213> ORGANISM: Homo sapiens

<400> SEQUENCE: 6

His Cys Arg His Asn Cys His Arg
1               5

```
<210> SEQ ID NO 7
<211> LENGTH: 6
<212> TYPE: PRT
<213> ORGANISM: Homo sapiens

<400> SEQUENCE: 7

His Cys Arg Cys His Arg
 1               5
```